(12) United States Patent
Yanagihara

(10) Patent No.: US 10,973,390 B2
(45) Date of Patent: Apr. 13, 2021

(54) WIRELESS ENDOSCOPE AND WIRELESS ENDOSCOPE SYSTEM

(71) Applicant: Olympus Corporation, Hachioji (JP)

(72) Inventor: Erika Yanagihara, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/677,484

(22) Filed: Nov. 7, 2019

(65) Prior Publication Data

US 2020/0069149 A1 Mar. 5, 2020

Related U.S. Application Data

(63) Continuation of application No. PCT/JP2018/015113, filed on Apr. 10, 2018.

(30) Foreign Application Priority Data

May 10, 2017 (JP) .............................. JP2017-094239

(51) Int. Cl.
| | | |
|---|---|---|
| *A61B 1/00* | (2006.01) | |
| *H04N 5/232* | (2006.01) | |
| *A61B 1/04* | (2006.01) | |
| *A61B 1/06* | (2006.01) | |
| *H04N 7/18* | (2006.01) | |
| *H04N 5/225* | (2006.01) | |

(52) U.S. Cl.
CPC ...... *A61B 1/00036* (2013.01); *A61B 1/00006* (2013.01); *A61B 1/00016* (2013.01);
(Continued)

(58) Field of Classification Search
CPC ............ A61B 1/00036; A61B 1/00006; A61B 1/00016; A61B 1/00027; A61B 1/04;
(Continued)

(56) References Cited

U.S. PATENT DOCUMENTS

| | | | | |
|---|---|---|---|---|
| 2005/0234774 A1* | 10/2005 | Dupree | .............. | G06Q 30/0272 705/14.57 |
| 2007/0066868 A1* | 3/2007 | Shikii | ................ | A61B 1/00036 600/118 |

(Continued)

FOREIGN PATENT DOCUMENTS

| | | |
|---|---|---|
| JP | 2001-037719 | 2/2001 |
| JP | 2003-144385 | 11/2001 |
| JP | 2005-080694 | 3/2005 |
| JP | 2005-110932 | 4/2005 |

(Continued)

OTHER PUBLICATIONS

International Search Report and Written Opinion from corresponding International Application No. PCT/JP2018/015113, dated Jul. 10, 2018.

*Primary Examiner* — Tracy Y. Li
(74) *Attorney, Agent, or Firm* — Oliff PLC

(57) ABSTRACT

An endoscope includes an insertion portion having a light source portion configured to emit illuminating light therefrom when inserted into a body cavity. An imaging portion is configured to capture an image in the body cavity. A transmission portion configured to transmit the image captured by the imaging portion. A battery is configured to supply electric power needed for endoscopic observation. A power control portion is configured to selectively control a supply of electric power to all of the light source portion, the imaging portion, and the transmission portion in a standby mode in which power consumption is reduced compared with a normal operation mode in which a supply of electric power is performed from the battery to all of the light source portion, the imaging portion, and the transmission portion.

19 Claims, 16 Drawing Sheets

(52) U.S. Cl.
CPC ............ *A61B 1/00027* (2013.01); *A61B 1/04* (2013.01); *A61B 1/06* (2013.01); *H04N 5/232411* (2018.08); *H04N 7/183* (2013.01); *H04N 2005/2255* (2013.01)

(58) Field of Classification Search
CPC ... A61B 1/06; A61B 1/00009; A61B 1/00108; A61B 1/00032; A61B 1/045; H04N 5/232411; H04N 7/183; H04N 2005/2255; G02B 23/24
See application file for complete search history.

(56) References Cited

U.S. PATENT DOCUMENTS

| | | | |
|---|---|---|---|
| 2008/0103356 A1 | 5/2008 | Minai et al. | |
| 2009/0163771 A1* | 6/2009 | Kimoto | A61B 1/00016 600/118 |
| 2016/0080652 A1* | 3/2016 | Shirota | H04N 7/183 348/222.1 |
| 2017/0231471 A1 | 8/2017 | Nishio et al. | |
| 2017/0251904 A1 | 9/2017 | Kasumi | |

FOREIGN PATENT DOCUMENTS

| | | |
|---|---|---|
| JP | 2008-113756 | 5/2008 |
| JP | 2010-184054 | 8/2010 |
| JP | 2012-011054 | 1/2012 |
| JP | 2013-094318 | 5/2013 |
| JP | 2014-054314 | 3/2014 |
| WO | 2016071992 | 5/2016 |
| WO | 2017029839 | 2/2017 |

* cited by examiner

F I G. 9

HIGHER POWER CONSUMPTION
FASTER RETURN

| MODE | DETAILS | IMAGING PORTION | LIGHT-SOURCE PORTION | IMAGE PROCESSING PORTION | WIRELESS COMMUNICATION PORTION |
|---|---|---|---|---|---|
| NORMAL OPERATION MODE | POWER IS SUPPLIED TO ALL CONFIGURATION ELEMENTS. | ○ | ○ | ○ | ○ |
| MODE 1 | ENDOSCOPIC IMAGE IS COMPRESSED MOST STRONGLY, AND TRANSMITTED. | ○ | ○ | ○ | ○ |
| MODE 2 | FULL BLACK IMAGE IS COMPRESSED AND TRANSMITTED. LIGHT SOURCE OR LED IS TURNED ON TO NOTIFY POWER-ON OF SCOPE. | × | ○ | ○ | ○ |
| MODE 3 | INSTEAD OF ENDOSCOPIC IMAGE, FULL BLACK IMAGE IS COMPRESSED AND TRANSMITTED (WITHOUT TURNING ON LIGHT SOURCE OF LED). | × | × | ○ | ○ |
| MODE 4 | ONLY TEXT DATA IS TRANSMITTED. | × | × | × | ○ |
| MODE 5 | RECEIVER ID IS STORED IN MEMORY, AND POWER SOURCE FOR ENTIRE SCOPE IS TURNED OFF (PAIRING IS DISCONNECTED). | × | × | × | × |

LOWER POWER CONSUMPTION
SLOWER RETURN

WIRELESS ENDOSCOPE AND WIRELESS ENDOSCOPE SYSTEM

CROSS-REFERENCE TO RELATED APPLICATIONS

This application is a continuation application of PCT Application No. PCT/JP2018/015113 filed on Apr. 10, 2018, which in turn claim priority to the Japanese Patent Application No. 2017-94239 filed on May 10, 2017 in Japan which is hereby incorporated by reference in its entirety.

TECHNICAL FIELD

The disclosed technology relates to a wireless endoscope and/or a wireless endoscope system capable of being activated by a battery.

DESCRIPTION OF THE RELATED ART

Endoscopes configured to observe an operation site in medical practice such as surgeries have found widespread utility in recent years. Surgeries and examinations are now often performed using such an endoscope. For example, surgeries under endoscopy, in which an endoscope is inserted into a body cavity such as the abdominal cavity or the thoracic cavity through a small fistula opened in the body surface of a patient and treatment or the like of an organ in the body cavity is performed under observation through the endoscope, and endoscopic examinations used, for example, in otolaryngologic diagnoses.

An endoscopic image in a body cavity of a patient as acquired by an imaging device of such an endoscope can be transmitted to a processor that performs processing of signals. The processor performs signal processing of the image from the endoscope, and supplies the resulting image signals as display signals to a monitor and also supplies them as recording signals to a recording device. In this manner, the endoscopic image can be shared among surgery-related personnel such as a surgeon, assistants, and nurses.

For the transmission of the endoscopic image from the endoscope to the processor, a scope cable is used. However, the scope cable may restrict the movable range of the endoscope or may interfere with the operability of the endoscope. In addition, the scope cable may tangle with other cables to cause problems such as disconnection. With the foregoing in view, wireless endoscopes have been developed in recent years. These endoscopes include a rechargeable battery mounted thereon and wirelessly transmit endoscopic images to a processor and the like.

Taking the portability into consideration, a limitation is imposed on the weight of a battery to be mounted on a wireless endoscope, and also on the capacity of the battery. Power saving is therefore required in wireless endoscopes.

In Japanese Patent—JP 2013-94318A, an electronic endoscope is disclosed. This electronic endoscope detects a use state or a disuse state and, if the disuse state is detected, power supply stops to imaging means.

According to the proposal of Japanese Patent—JP 2013-94318A, however, the power supply to the imaging means is controlled by detecting only a use state or a disuse state, so that significant power saving cannot be fully achieved. If the power supply to the endoscope is completely stopped in a disuse state, a need arises for power-on operation of a power source and various settings upon supplying electric power from a battery again. In some instances, cumbersome work and a relatively long time may hence be needed until acquisition of an endoscopic image. Especially at a wireless communication portion, a relatively long time may be required for the establishment of communication with a counterpart device, thereby possibly interfering the progress of surgical procedures for a long time.

BRIEF SUMMARY OF EMBODIMENTS

One aspect of the disclosed technology is directed to an endoscope includes an insertion portion having a light source portion configured to emit illuminating light therefrom when inserted into a body cavity. An imaging portion is configured to capture an image in the body cavity. A transmission portion configured to transmit the image captured by the imaging portion. A battery is configured to supply electric power needed for endoscopic observation. A power control portion is configured to selectively control a supply of electric power to all of the light source portion, the imaging portion, and the transmission portion in a standby mode in which power consumption is reduced compared with a normal operation mode in which a supply of electric power is performed from the battery to all of the light source portion, the imaging portion, and the transmission portion.

Another aspect of the disclosed technology is directed to an endoscope includes an insertion portion having a light source portion configured to emit illuminating light therefrom when inserted into a body cavity. An imaging portion is configured to capture an image in the body cavity. A transmission portion configured to transmit the image captured by the imaging portion. A battery is configured to supply electric power needed for endoscopic observation. A power control portion is configured to selectively control a supply of electric power to all of the light source portion, the imaging portion, and the transmission portion in a standby mode in which power consumption is reduced compared with a normal operation mode in which a supply of electric power is performed from the battery to all of the light source portion, the imaging portion, and the transmission portion. A processor is configured to receive the captured image by performing communication with the transmission portion.

A further aspect of the disclosed technology a method of operating an endoscope system using a non-transitory image processing program product having computer program code encoded thereon that when executed by a processor of a computer causes the computer to perform the operations of power supply in the endoscope system, the method comprising: transitioning to a standby mode in which power supply destinations are selectively decreased from a light source portion, an imaging portion, a transmission portion, and a plurality of circuit portions to reduce power consumption compared with a normal operation mode in which a supply of electric power is performed from a battery to all of the light source portion, the imaging portion, the transmission portion, and the circuit portions, and returning from the standby mode to the normal operation mode.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 9 is a table for explaining standby modes in the second embodiment.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has as objects thereof the provision of a wireless endoscope and a wireless endoscope system. The wireless endoscope has a normal operation mode and a plurality of standby modes provided beforehand, and can achieve both a quick return to a normal operation mode and low power consumption by switching the standby modes according to the use environment of the endoscope.

With reference to the drawings, a description will hereinafter be made in detail about embodiments of the disclosed technology.

First Embodiment

Figure 1:
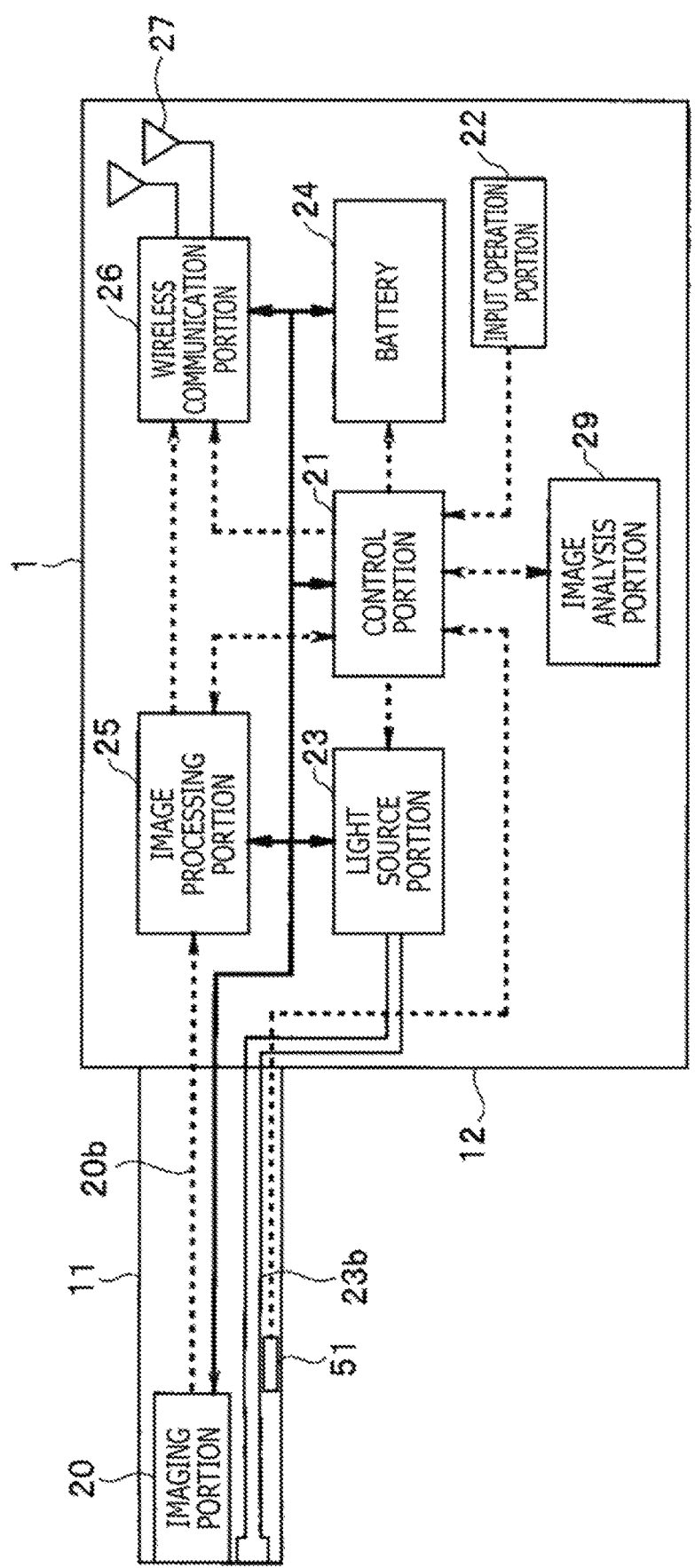
FIG. 1 is a block diagram illustrating a wireless endoscope according to a first embodiment of the disclosed technology.
Figure 2:
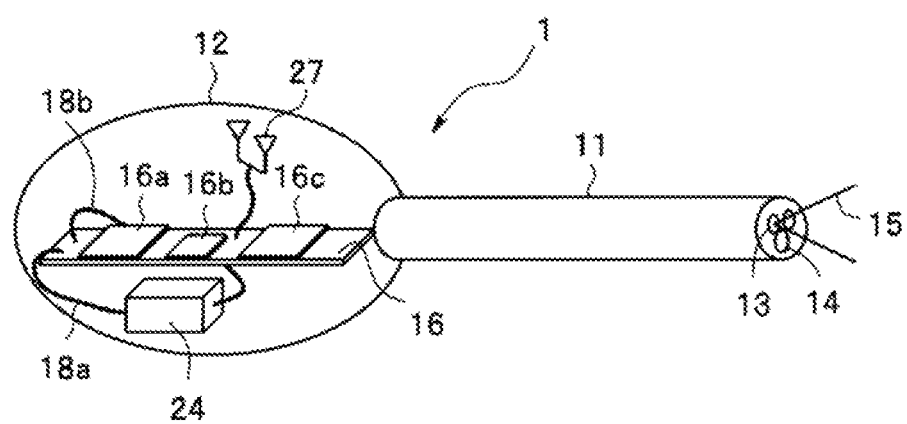
FIG. 2 is an explanatory view illustrating an outline of the wireless endoscope of FIG. 1.
Figure 3:
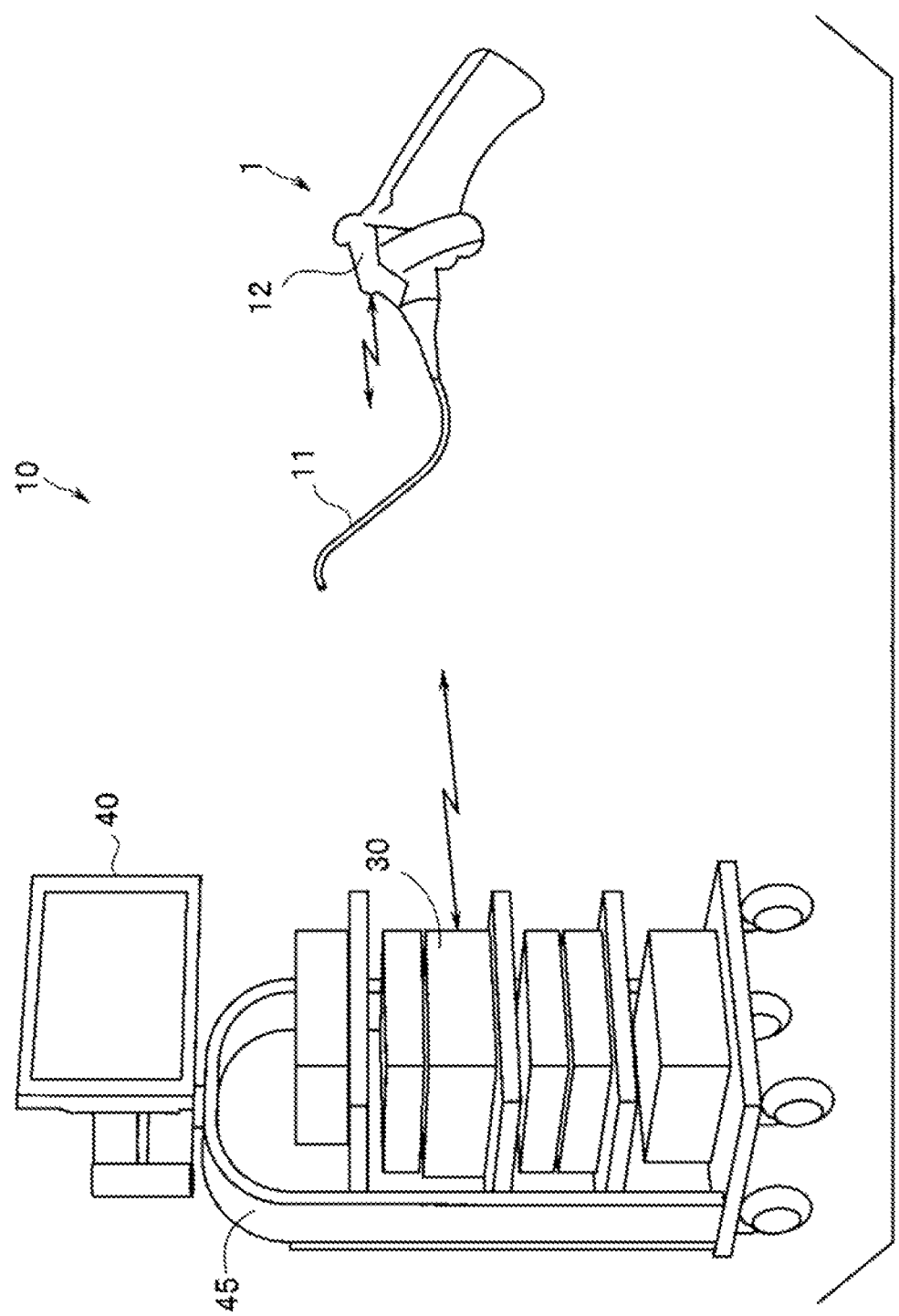
FIG. 3 is an explanatory view illustrating an overall configuration of a wireless endoscope system disposed in an operating room.
Figure 4:
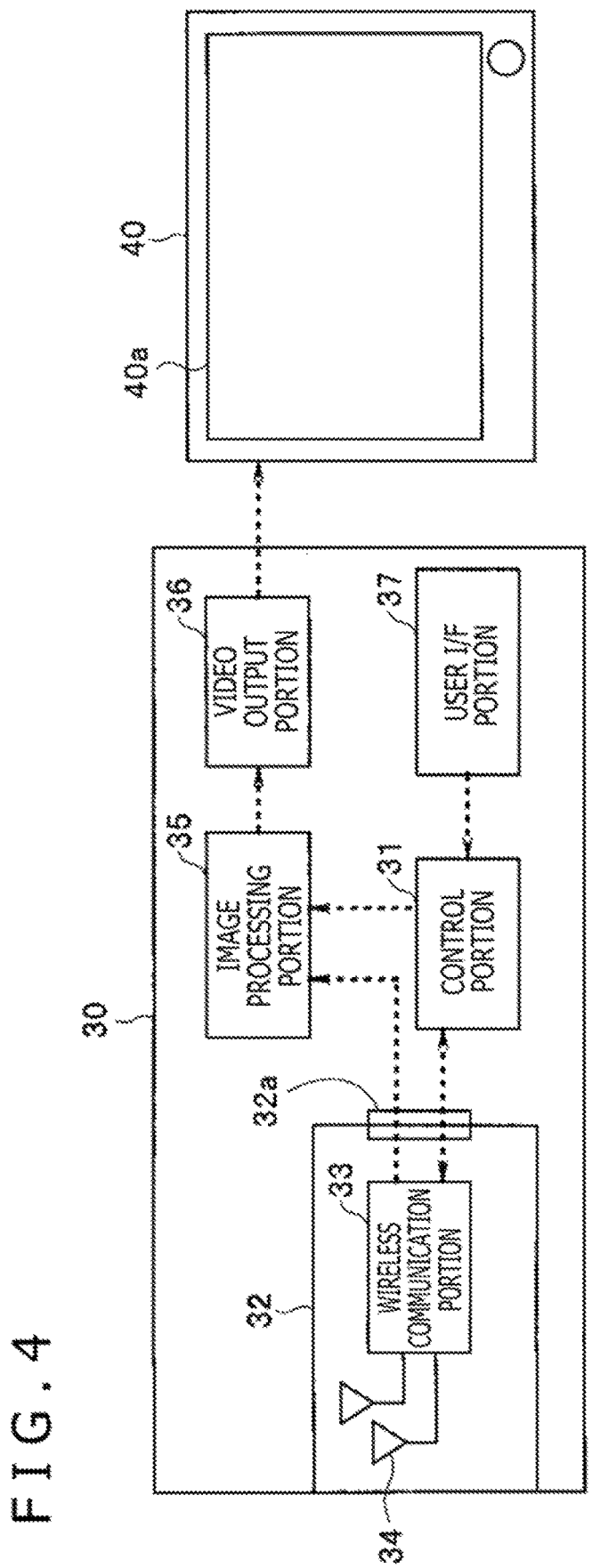
FIG. 4 is a block diagram illustrating an example of a specific configuration of a processor 30 in FIG. 3.

FIG. 1 is a block diagram illustrating a wireless endoscope according to a first embodiment of the disclosed technology. FIG. 2 is an explanatory view illustrating an outline of the wireless endoscope of FIG. 1. FIG. 3 is an explanatory view illustrating an overall configuration of a wireless endoscope system disposed in an operating room. FIG. 4 is a block diagram illustrating an example of a specific configuration of a processor 30 in FIG. 3.

Referring to FIGS. 2 to 4, a description will first be made about the outline of the endoscope system that uses the wireless endoscope.

As illustrated in FIG. 3, the endoscope system 10 is configured of the wireless endoscope 1, the processor 30, and a monitor 40. As illustrated in FIG. 3, a variety of medical devices and the monitor 40 are disposed on a cart 45 in the operating room. On the cart 45, the processor 30 is mounted. As illustrative medical devices, devices such as an electric cautery device, an insufflator, and a video recorder, a gas cylinder filled with carbon dioxide, and the like are also mounted on the cart 45.

The wireless endoscope 1 and the processor 30 are configured to enable wireless communication to one another via wireless communication portions 26 and 33 to be described hereinafter. Owing to mounting of a battery 24 to be described hereinafter, the wireless endoscope 1 is configured to enable imaging operation for normal endoscopic observation when activated by the battery. The wireless endoscope 1 has a wireless configuration to be wirelessly connected to the processor 30.

As illustrated in FIG. 2, the wireless endoscope 1 is configured having an insertion portion 11 on a distal end side and an operating portion 12 on a proximal end side. An imaging portion 20 (illustration omitted in FIGS. 2 and 3), which has an imaging device configured of a charge coupled device (CCD) or a complementary metal-oxide semiconductor (CMOS) sensor, is disposed in a distal end portion of the insertion portion 11. Further, a light source portion 23 (illustration omitted in FIGS. 2 and 3), which generates illuminating light to illuminate an object, is arranged in the operating portion 12. The wireless endoscope 1 is also configured so that light generated by the light source portion 23 is guided to a distal end of the insertion portion 11 and is illuminated as illuminating light 15 to the object via a lens 13.

The wireless endoscope 1 is configured so that return light from the object enters through the lens 14 at the distal end of the insertion portion 11 and is focused on an imaging surface in the imaging portion 20. By photoelectric conversion, the imaging portion 20 acquires a captured image based on an optical image of the object. The imaging portion 20 is configured to transmit the captured image to a substrate 16 in the operating portion 12 via a signal line 20b in the insertion portion 11. On the substrate 16 arranged in the operating portion 12, various integrated circuits (ICs) 16a to 16c are mounted. Individual circuit portions in FIG. 1 are configured of these ICs 16a to 16c and the like.

The imaging portion 20 has been described as being arranged at the distal end of the insertion portion 11. As an alternative, however, the imaging portion 20 may be disposed like a camera head on the side of the operating portion 12, or the light source portion 23 may be disposed in the insertion portion 11 to emit illuminating light from the distal end of the insertion portion 11.

The battery 24 is disposed as a power source in the operating portion 12. The wireless endoscope 1 is configured to enable a supply of electric power from the battery 24 to the individual circuit portions, which are mounted on the substrate 16, via power lines 18a and 18b connected to the battery 24.

In FIG. 4, the processor 30 is configured to enable detachable attachment of the wireless communication portion 33 to an attachment base 32. The wireless communication portion 33 is electrically connected to a control portion 31 and an image processing portion 35 via a connector 32a. It is to be noted that such a wireless device may be built in the processor 30 instead of the detachable configuration.

The wireless communication portion 33 can perform wireless communication with the wireless communication portion 26 of the wireless endoscope 1, for example, at 5 GHz bandwidth or 60 GHz bandwidth. The wireless communication portion 33 performs transmission and reception of image signals and various information to be transmitted and received at 5 GHz bandwidth or 60 GHz bandwidth via an antenna 34.

The wireless communication portion 33 feeds the image processing portion 35 with each captured image so received. In addition, the wireless communication portion 33 can feed the control portion 31 with various information from the wireless endoscope 1 and can also transmit various information from the control portion 31 to the wireless endoscope 1 via the antenna 34.

Under control by the control portion 31, the image processing portion 35 applies predetermined image processing to the captured image so inputted, and then outputs the resulting captured image to a video output portion 36. The video output portion 36 converts the inputted captured image to a format that can be displayed on the monitor 40, and then outputs the formatted captured image to the monitor 40. The monitor 40 acquires the captured image from the video output portion 36, and subsequent to application of predetermined image processing, displays the resulting captured image on a display screen 40a. In this manner, the image captured by the imaging portion 20 is displayed as a video image or still image on the display screen 40a.

A user interface (I/F) portion 37 is an interface for receiving user's operation. For example, the user I/F portion 37 is configured of a front panel, various buttons in a control system, and the like, and outputs, to the control portion 31, operation signals based on user's operation. Via the user I/F portion 37, a variety of user's operations such as the designation of an observation mode for the wireless endoscope 1 and setting relating to the display of an image can be received. For example, based on operation signals from the user I/F portion 37, the control portion 31 can give deliver various instructions to a control portion 21 of the wireless endoscope 1 via the wireless communication portions 33 and 26.

In FIG. 1, power supply lines are indicated by solid lines, and signal transmission lines are indicated by broken lines. In FIG. 1, the control portion 21 is arranged in the wireless endoscope 1. The control portion 21 can be configured of a processor that used an unillustrated central processing unit (CPU) or the like, and may be configured to enable control of the individual portions according to a program stored in a memory or storage portion. An input operation portion 22 is configured of an unillustrated mechanical switch, lever or the like, and is configured to supply the control portion 21 with operation signals based on user's operation.

The battery 24 generates electric power needed for endoscopic observation. For example, the battery 24 generates electric power to be supplied to the control portion 21, the light source portion 23, an image processing portion 25, the wireless communication portion 26, the imaging portion 20, and an image analysis portion 29 of the wireless endoscope 1. The light source portion 23 receives a supply of electric power from the battery 24 and under control by the control portion 21, generates light to illuminate an object. This illuminating light is transmitted to the distal end portion of the insertion portion 11 via a light guide 23b inserted through the insertion portion 11. Upon receipt of electric power supplied from the battery 24, the imaging portion 20 is activated by the control portion 21 to capture an image of the object, and outputs the captured image to the image processing portion 25 via the signal line 20b.

Upon receipt of electric power supplied from the battery 24, the image processing portion 25 applies predetermined image processing to the captured image from the imaging portion 20, and then outputs the resulting image to the wireless communication portion 26. The image processing portion 25 can perform, for example, image compression processing as the image processing. The wireless communication portion 26, which is a communication portion, receives a supply of electric power from the battery 24, and under activation by the control portion 21, wirelessly transmits the processed captured image to the processor 30 or the like.

The wireless communication portions 26 and 33 perform communication with each other by adopting a predetermined wireless transmission path, for example, a wireless local area network (LAN) such as wireless fidelity (Wi-Fi) (registered trademark). The wireless communication portions 26 and 33 are configured to be fed with default information from the control portion 21 and to perform pairing processing according to the default so that communication is established with each other. There can be many wireless devices in the operating room. The wireless communication portions 26 and 33 search for a vacant channel to enable securement of a necessary bandwidth without interference, and establish communication while changing connection settings as needed. In some instances, the wireless communication portions 26 and 33 hence may not be able to establish reliable communication for the transmission of an image if the default information from the control portion 21 is solely used. Accordingly, the wireless communication portion 26 not only may require a relatively long time when performing an establishment of communication or pairing at first after power-on but also may require a relatively long time upon performing pairing again after the communication is interrupted once or the pairing is disconnected.

In this embodiment, the control portion 21 is configured to control each portion in three operation modes consisting of a normal operation mode, a standby mode A, and a standby mode B as will be mentioned hereinafter. The normal operation mode supplies electric power from the battery 24 to all the circuit portions of the wireless endoscope 1 as much as needed. The standby mode A and standby mode B are to be set when the wireless endoscope 1 is not used in the observation of a subject, are configured to reduce power consumption compared with the normal operation mode, and, for example, are configured to limit the supply of electric power from the battery 24 to the individual circuit portions.

Figure 5:
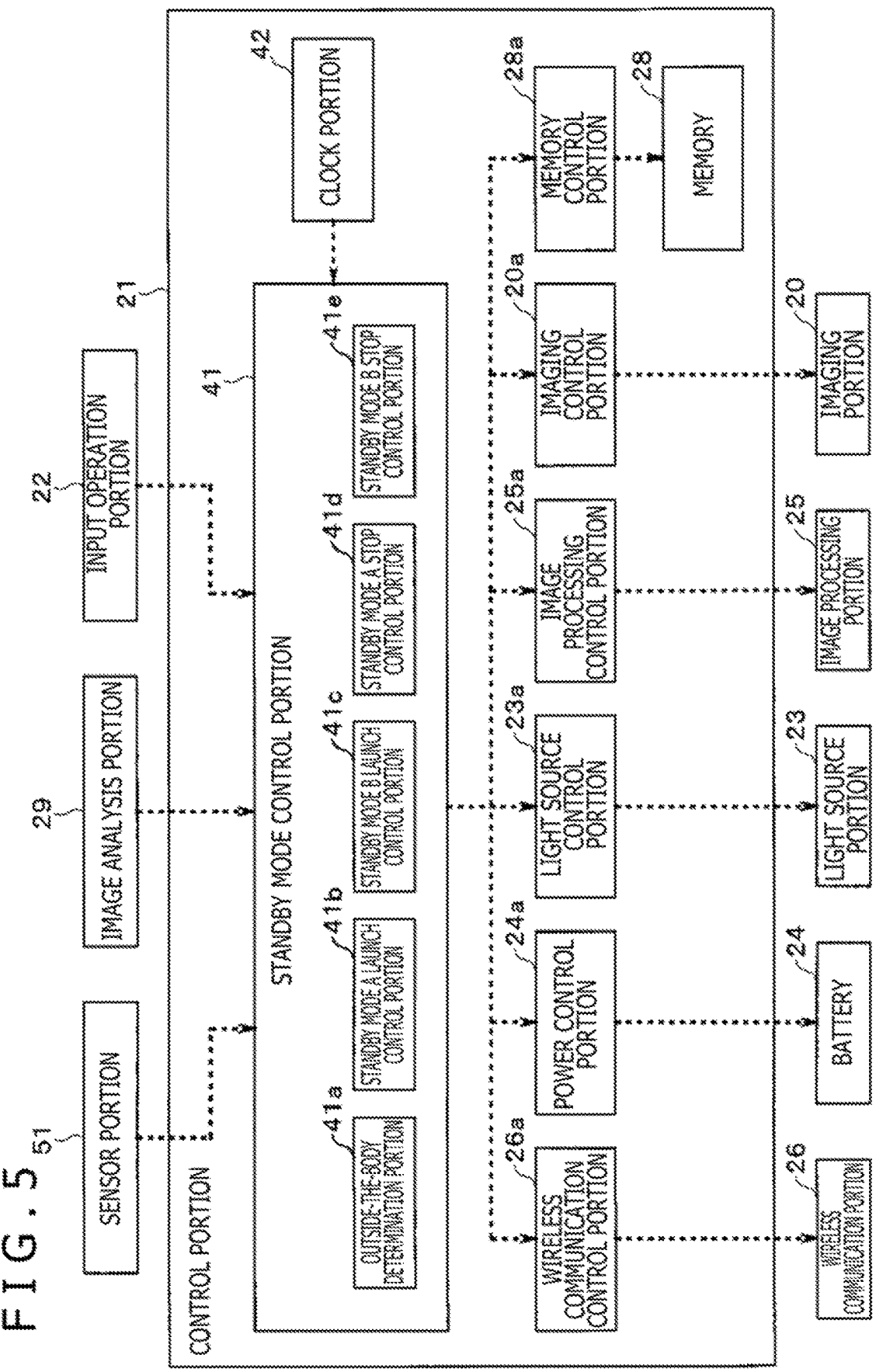
FIG. 5 is a block diagram illustrating an example of a functional block of a control portion 21 in FIG. 1.

FIG. 5 is a block diagram illustrating an example of a functional block of the control portion 21 in FIG. 1.

In this embodiment, the control portion 21 performs control in the standby mode A to enable suppression of the battery consumption and also return to the normal operation mode in a short time. In the standby mode B, on the other hand, the control portion 21 performs control to supply minimum necessary electric power to only the necessary circuit portion or portions so that the battery consumption is significantly suppressed.

The control portion 21 has a standby mode control portion 41, a clock portion 42, a wireless communication control portion 26a, a power control portion 24a, a light source control portion 23a, an image processing control portion 25a, an imaging control portion 20a, and a memory control portion 28a. The clock portion 42 outputs time information to the standby mode control portion 41. The wireless communication control portion 26a, power control portion 24a, light source control portion 23a, image processing control portion 25a, imaging control portion 20a, and memory control portion 28a are configured to control the wireless communication portion 26, battery 24, light source portion 23, image processing portion 25, imaging portion 20, and a memory 28, respectively.

The standby mode control portion 41 of the control portion 21 includes an outside-the-body determination portion 41a, a standby mode A launch control portion 41b, a standby mode B launch control portion 41c, a standby mode A stop control portion 41d, and a standby mode B stop control portion 41e. The outside-the-body determination portion 41a is configured to make a determination as to whether or not the insertion portion 11 is inserted in the body or the insertion portion 11 is placed outside the body (hereinafter called "inside-the-body determination" or "outside-the-body determination"), and to obtain a determination result. The standby mode A launch control portion 41b makes a determination of transition to the standby mode A and performs setting of the standby mode A, while the standby mode B launch control portion 41c makes a determination of transition to the standby mode B and performs setting of the standby mode B. Further, the standby mode A stop control portion 41d makes a determination of return from the standby mode A to the normal operation mode and performs processing to return to the normal operation mode, while the standby mode B stop control portion 41e makes a determination of return from the standby mode B to the normal operation mode and performs processing for return to the normal operation mode.

For example, the standby mode A launch control portion 41b may perform control to reduce power consumption in the standby mode A by giving instructions to the image processing control portion 25a and wireless communication portion 26 so that the compression ratio in image compression processing at the image processing portion 25 is made higher than that in the normal operation mode to decrease the transmission volume of an image from the wireless communication portion 26 compared with the normal operation mode. As an alternative, the standby mode A launch control portion 41b may give an instruction to the power control portion 24a in the standby mode A to stop a supply of electric power to the imaging portion 20, to stop a supply of electric power to the light source portion 23, and/or to stop a supply of electric power to the image processing portion 25. Further, the standby mode A launch control portion 41b may control the imaging control portion 20a in the standby mode A so that the imaging portion 20 is controlled to a lower imaging rate than that in the normal operation mode. Furthermore, the standby mode A launch control portion 41b may give an instruction to the light source control portion 23a in the standby mode A so that the light source portion 23 is controlled to be turned on during a suspension of imaging.

As mentioned hereinbefore, the wireless communication portion 26 requires a relatively long time when performing pairing again after pairing is disconnected. Once pairing is disconnected, a relatively long time is therefore required until returning to the normal operation mode. The standby mode A launch control portion 41b is thus configured to perform control so that no disconnection of pairing is made in the standby mode A. For example, the standby mode A launch control portion 41b is configured to maintain a paired state in the standby mode A by controlling the wireless communication portion 26 to transmit certain data such as an endoscopic image, a high-compression endoscopic image, a black image, header information or a control frame.

On the other hand, the standby mode B launch control portion 41c may be configured to give an instruction to the power control portion 24a in the standby mode B so that the supply of electric power to all of the wireless communication portion 26, the light source portion 23, the image processing portion 25, and the imaging portion 20 is stopped. In this case, pairing is also disconnected accordingly. Further, the standby mode B launch control portion 41c is configured to control the memory control portion 28a so that, when transferring to the standby mode B, information regarding communication setting such as a receiver identification (ID) upon pairing of the wireless communication portion 26 is stored in the memory 28. The standby mode B stop control portion 41e is configured to perform pairing in a relatively short time by reading the information regarding communication setting stored in the memory 28 and setting the same at the wireless communication portion 26 when returning from the standby mode B to the normal operation mode.

The standby mode A launch control portion 41b may also be configured to perform switching of the operation modes based on a determination (hereinafter called "outside-the-body determination") as to whether or not the insertion portion 11 of the endoscope is inserted in the body or whether or not the insertion portion 11 is placed outside the body. For example, the outside-the-body determination portion 41a may determine the placing of insertion portion 11 outside the body by detecting that a user has operated an unillustrated switch in the input operation portion 22.

In the insertion portion 11 of the wireless endoscope 1, a sensor portion 51 having one or plural kinds of sensors is disposed. For example, various sensors such as a temperature sensor, a humidity sensor, a motion sensor, an acceleration sensor, and a gyro sensor may be disposed in the sensor portion 51. The sensor portion 51 is configured to output detection results of one or more sensors to the standby mode control portion 41 of the control portion 21. If a temperature sensor or a humidity sensor is disposed in the sensor portion 51, for example, the outside-the-body determination portion 41a of the standby mode control portion 41 may determine, based on a detection result of temperature or humidity, whether or not the insertion portion 11 is placed outside the body.

The wireless endoscope 1 also includes the image analysis portion 29. Through an image analysis, for example, an analysis of the luminance or color of an image captured by the imaging portion 20, the image analysis portion 29 determines whether the image is an image inside the body of a subject or an endoscopic image or an image outside the body of the subject. For example, the image analysis portion 29 feeds the standby mode control portion 41 with a determination result as to whether or not the image captured by the imaging portion 20 is evenly tinged with red. If the degree of the reddish tinge of the captured image (for example, the number of reddish pixels on a screen) is higher or greater than a predetermined threshold, the outside-the-body determination portion 41a of the standby mode control portion 41 may determine that the insertion portion 11 is inserted in the body.

The standby mode control portion 41 may also be configured to perform switching of the operation modes based on a determination as to whether or not the insertion portion 11 of the wireless endoscope 1 has been left out of use for observation (hereinafter called "left-out-of-use determination"). For example, the standby mode control portion 41 may perform a left-out-of-use determination based on a determination result as to whether or not the amount of movement in an endoscopic image from the imaging portion 20 is greater than a predetermined threshold. The standby mode control portion 41 determines to be left out of use if the amount of movement is smaller than the predetermined threshold. If the sensor portion 51 has a motion sensor or acceleration sensor, the standby mode control portion 41 may also determine, based on a detection result of the motion sensor or acceleration sensor that the insertion portion 11 is not moved and is left out of use.

The standby mode control portion 41 may also be configured to perform switching of the operation modes based on a determination (hereinafter called "return determination") as to whether or not the insertion portion 11 of the wireless endoscope 1 has been put into use for observation from the left-out-of-use state. For example, the standby mode control portion 41 may make a return determination based on user's operation at the input operation portion 22. The standby mode control portion 41 may also make a return determination if the amount of movement in the endoscopic image from the imaging portion 20 is greater than the predetermined threshold. If the sensor portion 51 has a motion sensor or acceleration sensor, the standby mode control portion 41 may also determine a return by detecting, based on a detection result of the motion sensor or acceleration sensor that the insertion portion 11 has not been left out of use but is being moved.

For example, the standby mode A launch control portion 41b launches the standby mode A if the insertion portion 11 is determined to be placed outside the body by the outside-the-body determination portion 41a and the insertion portion 11 is determined by a left-out-of-use determination to be left out of use without being used for observation for a predetermined period of time. The standby mode B launch control portion 41c launches the standby mode B if the insertion portion 11 is determined to be placed outside the body by the outside-the-body determination portion 41a and a predetermined period of time has elapsed with the insertion portion 11 being left out of use after launch of the standby mode A.

The standby mode A stop control portion 41d stops the standby mode A to return to the normal operation mode if in the standby mode A, the insertion portion 11 is determined by the outside-the-body determination portion 41a to be inserted in the body or the insertion portion 11 is determined by a left-out-of-use determination to have been put into use for observation.

The standby mode B stop control portion 41e stops the standby mode B to return to the normal operation mode if in the standby mode B, the insertion portion 11 is determined by the outside-the-body determination portion 41a to be inserted in the body or the insertion portion 11 is determined by a left-out-of-use determination to have been put into use for observation.

Figure 6:
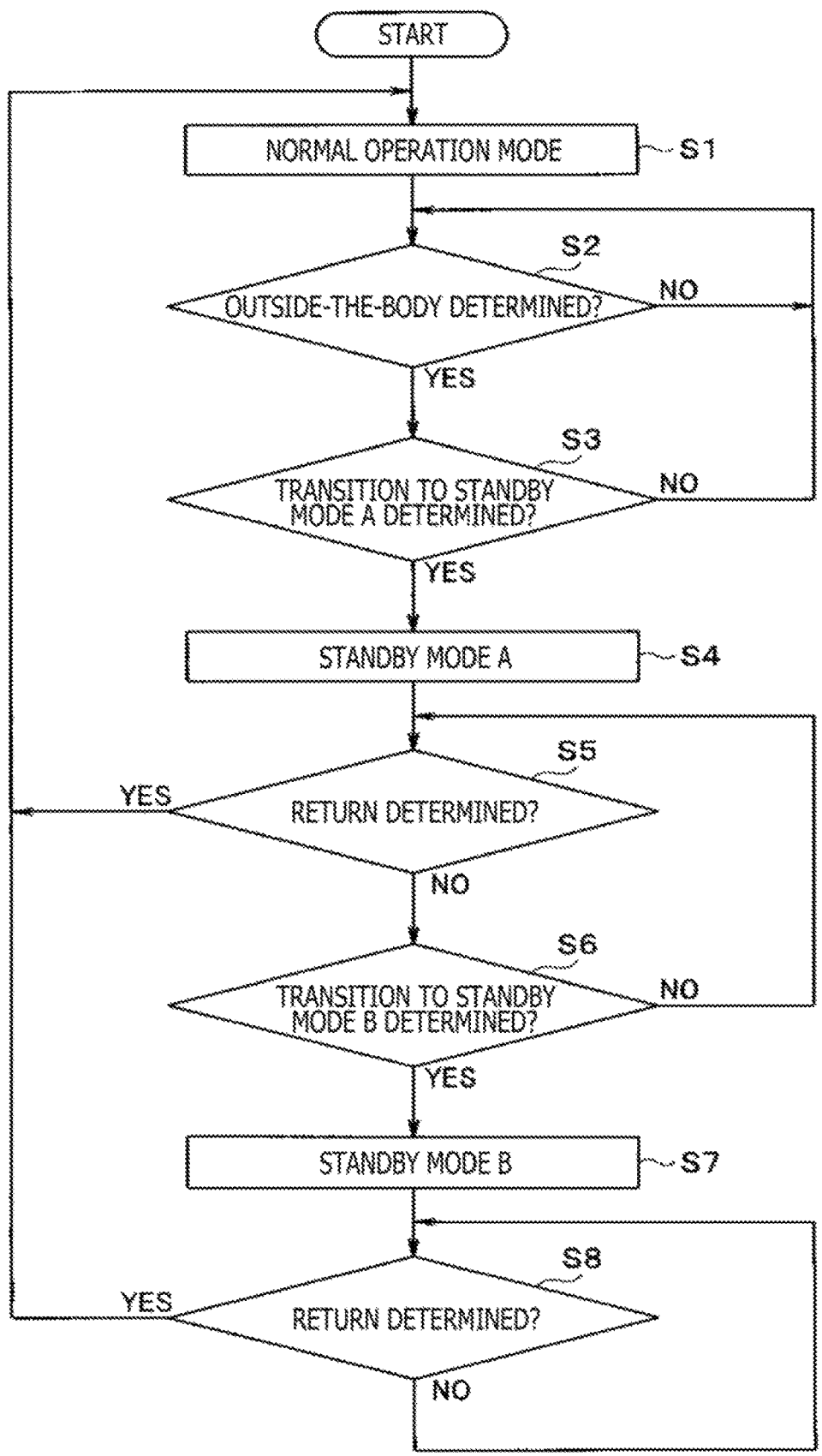
FIG. 6 is a flow chart for explaining operation of the first embodiment.
Figure 7:
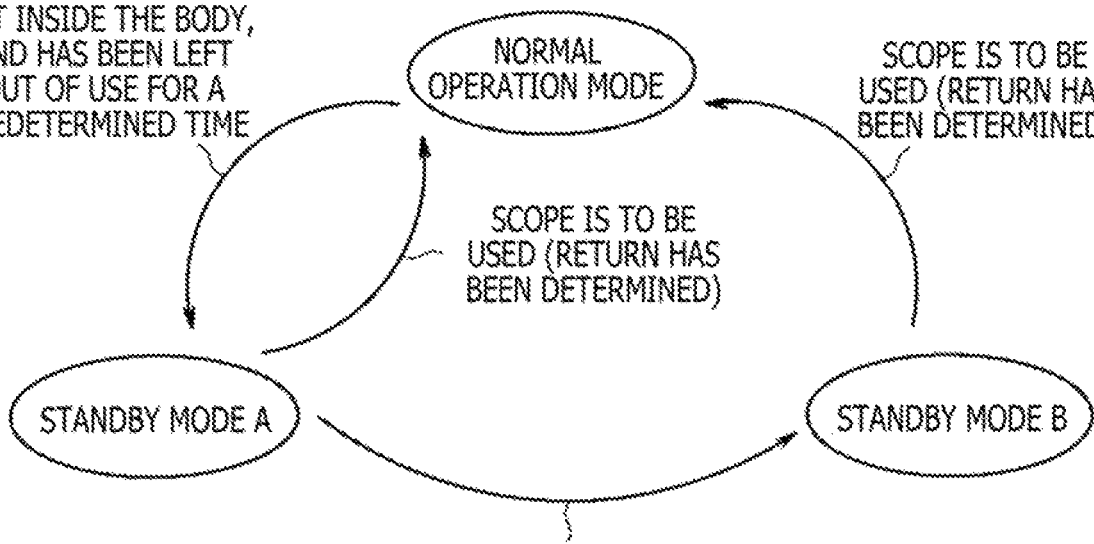
FIG. 7 is a state transition diagram for explaining the operation of the first embodiment.

With reference to FIGS. 6 and 7, a description will next be made about operation of the first embodiment configured as described hereinbefore. FIG. 6 is a flow chart for explaining the operation of the first embodiment. FIG. 7 is a state transition diagram for explaining the operation of the first embodiment.

In this embodiment, the wireless endoscope 1 is configured to operate in the three operation modes consisting of the normal operation mode, the standby mode A, and the standby mode B as illustrated in the state transition diagram of FIG. 7, and transitions are made between the individual operation modes according to the conditions presented in FIG. 7.

Described specifically, when the power source of the wireless endoscope 1 is turn on, the control portion 21 first sets the normal operation mode in step S1 in FIG. 6. The standby mode control portion 41 of the control portion 21 controls the power control portion 24a to supply electric power of the battery 24 to all the circuit portions in the wireless endoscope 1. In this manner, battery activation is started, so that imaging by the imaging portion 20 is performed. A captured image is subjected to image processing by the image processing portion 25 and is then transmitted to the processor 30 by the wireless communication portion 26.

Next, the standby mode control portion 41 of the control portion 21 makes an outside-the-body determination in step S2. The outside-the-body determination portion 41a makes an outside-the-body determination based on an operation signal from user's operation at the input operation portion 22, an image analysis result from the image analysis portion 29, or a detection result from the sensor portion 51. If the insertion portion 11 is determined to be placed outside the body, the processing proceeds to step S3. If the insertion portion 11 is determined to be inserted in the body, the outside-the-body determination in step S2 is repeated.

It is now assumed that a surgeon stops the observation by the wireless endoscope 1. For example, it is assumed that the surgeon pulls the insertion portion 11 out of the body and leaves it out of use outside the body. If the insertion portion 11 is determined, by the standby mode control portion 41, to be placed outside the body by the outside-the-body determination portion 41a, the standby mode A launch control portion 41b determines in step S3 whether or not the operation mode should transfer to the standby mode A. If the insertion portion 11 is left out of use outside the body for a predetermined period of time or longer after it has been pulled out of the body, for example, the standby mode A launch control portion 41b sets the standby mode A in step S4.

In the standby mode A, the standby mode A launch control portion 41b, for example, gives an instruction to the image processing control portion 25a to increase the compression ratio for the image compared with the normal operation mode, and/or gives an instruction to the power control portion 24a to stop the supply of electric power to the imaging portion 20, light source portion 23, image processing portion 25, and the like. By such processing, the power consumption can be reduced in the standby mode A compared with the normal operation mode.

The standby mode A launch control portion 41b is configured to give an instruction to the wireless communication control portion 26a in the standby mode A so that wireless communication to the processor 30 by the wireless communication portion 26 is continued.

In next step S5, the standby mode A stop control portion 41d makes a return determination from the standby mode A to the normal operation mode. If the wireless endoscope 1 or the scope is determined to have been used in the standby mode A, for example, such as in the case where the surgeon has inserted the insertion portion 11 into the body or has moved the insertion portion 11, which was left out of use outside the body, for use in observation in the body, the standby mode A stop control portion 41d returns the operation mode to the normal operation mode in step S1. For example, the standby mode A stop control portion 41d gives an instruction to the power control portion 24a to resume the supply of electric power to the individual portions of the wireless endoscope 1.

In the standby mode A, the wireless communication by the wireless communication portion 26 is still in continuation. It is therefore unnecessary to perform pairing processing again upon returning to the normal operation mode. The return to the normal operation mode is hence achieved in a short time.

In step S6, the standby mode B launch control portion 41c determines whether or not the operation mode should transfer to the standby mode B. If the insertion portion 11 has been continuously left out of use for a predetermined period of time since the start of the standby mode A or in a like case, the standby mode B launch control portion 41c sets the standby mode B in step S7.

For example, the standby mode B launch control portion 41c controls the memory control portion 28a in the standby mode B to store, in the memory 28, information regarding the wireless communication setting of the wireless communication portion 26, and then gives an instruction to the power control portion 24a to stop the supply of electric power to the imaging portion 20, light source portion 23, wireless communication portion 26, and image processing portion 25. By this processing, the power consumption can be reduced in the standby mode B compared with the standby mode A.

The control portion 21 is configured to also disconnect wireless communication with the processor 30 via the wireless communication portion 26 in the standby mode B. Although a relatively long time is needed to return to the normal operation mode, the supply of electric power to most of the circuit portions is stopped. It is therefore possible to significantly reduce the power consumption.

In next step S8, the standby mode B stop control portion 41e makes a return determination from the standby mode B to the normal operation mode. If the scope is determined to have been used in the standby mode B, for example, such as in the case where the surgeon has inserted the insertion portion 11 into the body or has moved the insertion portion 11, which was left out of use outside the body, for use in observation in the body, the standby mode B stop control portion 41e returns the operation mode to the normal operation mode of step S1. For example, the standby mode B stop control portion 41e gives an instruction to the power control portion 24a to resume the supply of electric power to the individual portions of the wireless endoscope 1. The standby mode B stop control portion 41e is configured to shorten pairing operation at the wireless communication portion 26 in this case by feeding the information regarding the wireless communication setting, which is stored in the memory 28, to the wireless communication portion 26.

If it is not determined by the standby mode B launch control portion 41c in step S6 that the operation mode should transfer to the standby B mode, the processing is returned to step S5, where the return determination is repeated. If it is determined by the standby mode B stop control portion 41e in step S8 that the operation mode should not return to the normal operation mode, the processing is returned to step S8, where the return determination is repeated.

As described hereinbefore, if the wireless endoscope 1 is not in a use state, the operation mode transfers to the standby mode A or the standby mode B to reduce the power consumption in this embodiment. In this case, for a predetermined period of time after the wireless endoscope 1 has been put into a disuse state in the normal operation mode, the standby mode A is set to maintain the paired state with the processor 30 so that the return to the normal operation mode is enabled in a short time. If the predetermined period of time has elapsed with the wireless endoscope 1 being left out of use, the operation mode transfers to the standby mode B in which the supply of electric power to the wireless communication portion 26 is also stopped and the paired state is cancelled, whereby a significant reduction of power consumption is enabled. In this manner, it is possible to obtain significant effects for the reduction of power consumption while shortening the time for the return to the normal operation mode. Moreover, if the insertion portion 11 is inserted in the body, control is performed to avoid transferring to any of the standby mode A or the standby mode B. This enables reliable imaging in a body cavity, and can prevent a failure to acquire an endoscopic image when needed.

In FIGS. 6 and 7, the example of transition from the standby mode A to the standby mode B is only illustrated. However, the operation mode may be configured to transition from the standby mode B to the standby mode A.

Second Embodiment

Figure 8:
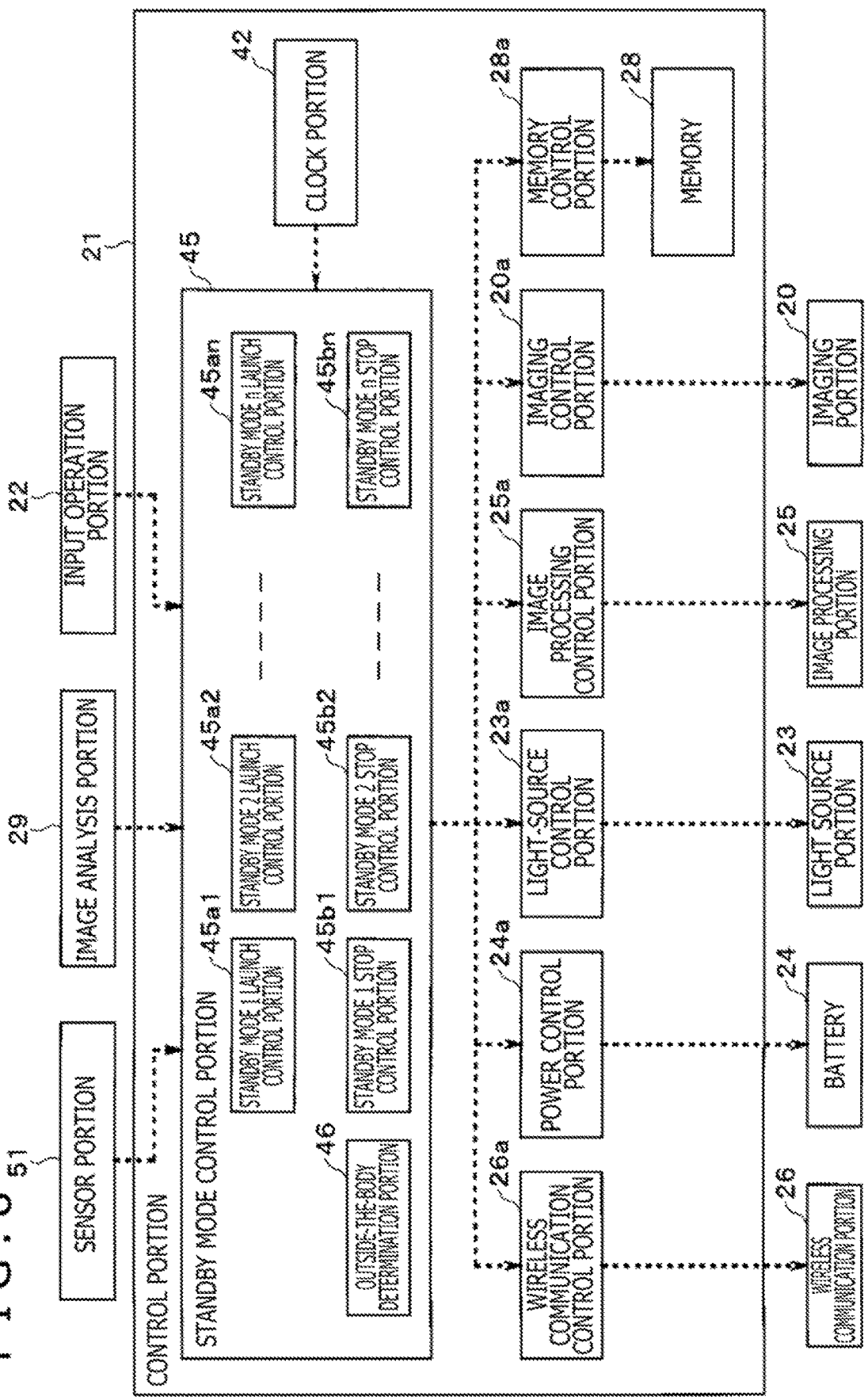
FIG. 8 is a block diagram illustrating a second embodiment of the disclosed technology.

FIG. 8 is a block diagram illustrating a second embodiment of the disclosed technology. In FIG. 8, the same elements as in FIG. 5 are identified by the same numeral references, and their description is omitted. This embodiment differs only in the functions of the control portion 21, and other hardware configurations are similar to the first embodiment.

In the first embodiment, the two standby modes are set, one being the standby mode A that, while maintaining a paired state between the wireless communication portions, reduces power consumption and shortens a return time to the normal operation mode, and the other the standby mode B that obtains significant effects for the reduction of power consumption by cancelling a paired state between the wireless communication portions. In this embodiment, on the other hand, the standby mode A is divided into plural modes to enable fine control of the effects for the reduction of power consumption and the effects for the shortening of the return time to the normal operation mode.

FIG. 9 is a table for explaining standby modes in the second embodiment. In FIG. 9, the marks ○ indicate that electric power is supplied, and the marks x indicate that electric power is not supplied.

FIG. 9 illustrates an example in which the standby mode is divided into standby mode 1 to standby mode 5. The standby mode 1 is to wirelessly transmit an endoscopic image after compressing it at a highest compression ratio. In this case, electric power is supplied to all of the imaging portion 20, light source portion 23, image processing portion 25, and wireless communication portion 26. In the standby mode 1, the power consumption at the wireless communication portion 26 can be reduced compared with the normal operation mode by increasing the compression ratio and lowering the transmission rate.

The standby mode 2 is to stop the supply of electric power to the imaging portion 20. In this manner, a compressed image of a full black, empty image is to be outputted from the image processing portion 25. This compressed image does not have image information and can significantly reduce the code amount, so that the standby mode 2 can reduce the power consumption at the wireless communication portion 26 compared with the standby mode 1. The standby mode 2 can also reduce the power consumption at the imaging portion 20 compared with the standby mode 1.

The wireless endoscope 1 and wireless endoscope system 10 may be configured to perform control such as turning on the light source portion 23 and turning on unillustrated light emitting diodes (LEDs) disposed in the processor 30 and wireless endoscope 1 in this mode for allowing the surgeon to recognize that the power source of the wireless endoscope 1 or the scope has been turned on. In the standby mode 2, the image data of the empty image has been transmitted from the wireless communication portion 26 to the processor 30, and the paired state is maintained.

The standby mode 3 is to stop the supply of electric power to the imaging portion 20 and light source portion 23. In this case, a compressed image of a full black and empty image is also to be outputted from the image processing portion 25. As the supply of electric power to the light source portion 23 is stopped, the power consumption can be considerably reduced compared with the standby mode 2. In the standby mode 3, the image data of the empty image has also been transmitted from the wireless communication portion 26 to the processor 30, and the paired state is also maintained.

The standby mode 4 is to stop the supply of electric power to the imaging portion 20, light source portion 23, and image processing portion 25. In this manner, the power consumption can be reduced in the standby mode 4 than the standby mode 3. No signals are outputted from the image processing portion 25 in the standby mode 4. In order to maintain a paired state with the processor 30, the control portion 21 therefore transmits packet data required to maintain the paired state, for example, predetermined data, e.g., text data, such as header information, a control frame, and address information to the wireless communication portion 26 according to a communication protocol. The paired state is hence maintained in the standby mode 4.

The standby mode 1 to the standby mode 4 correspond to the standby mode A in the first embodiment. The standby mode 5 corresponds to the standby mode B in the first embodiment, and as presented in FIG. 9, stops the supply of electric power not only to the imaging portion 20, light source portion 23, and image processing portion 25 but also to the wireless communication portion 26. In other words, the standby mode 5 turns off the power source for the entire endoscope other than the control portion 21. The control portion 21 is configured to store communication setting information such as the receiver ID, which the wireless communication portion 26 uses for communication, in the memory 28 in the standby mode 5 before stopping the supply of electric power to the wireless communication portion 26. Therefore, in the table of FIG. 9, the upper the row of mode, the faster the return, and the lower the row of mode, the smaller the power consumption.

In FIG. 8, the control portion 21 is different from the standby mode control portion 41 in FIG. 5 in only the function of the standby mode control portion 45. The standby mode control portion 45 is configured of an outside-the-body determination portion 46, a standby mode 1 launch control portion 45*a*1, a standby mode 2 launch control portion 45*a*2, . . . , a standby mode n launch control portion 45*an*, a standby mode 1 stop control portion 45*b*1, a standby mode 2 stop control portion 45*b*2, . . . , and a standby mode n stop control portion 45*bn*. The outside-the-body determination portion 46 has a similar function as the outside-the-body determination portion 41*a* in FIG. 5.

The standby mode 1 launch control portion 45*a*1, standby mode 2 launch control portion 45*a*2, . . . , and standby mode n launch control portion 45*an* make a launch determination or a determination as to a transition condition with respect to the standby modes 1, 2, . . . , and n, respectively, and perform transitions to the standby modes 1, 2, . . . , and n (n: integer), respectively. On the other hand, the standby mode 1 stop control portion 45*b*1, standby mode 2 stop control portion 45*b*2, . . . , and standby mode n stop control portion 45*bn* are configured to make a stop determination or a return determination with respect to the standby modes 1, 2, . . . , and n, respectively, and to return the operation mode to the normal operation mode.

FIG. 9 is an example of n=5, the standby mode 1 launch control portion 45*a*1 to the standby mode 5 launch control portion 45*a*5 are configured to perform the standby modes 1 to 5 in FIG. 9, respectively, and the standby mode 1 stop control portion 45*b*1 to the standby mode 5 stop control portion 45*b*5 are configured to make a stop determination with respect to the standby modes 1 to 5, respectively, and to return operation mode to the normal operation mode.

Figure 10:
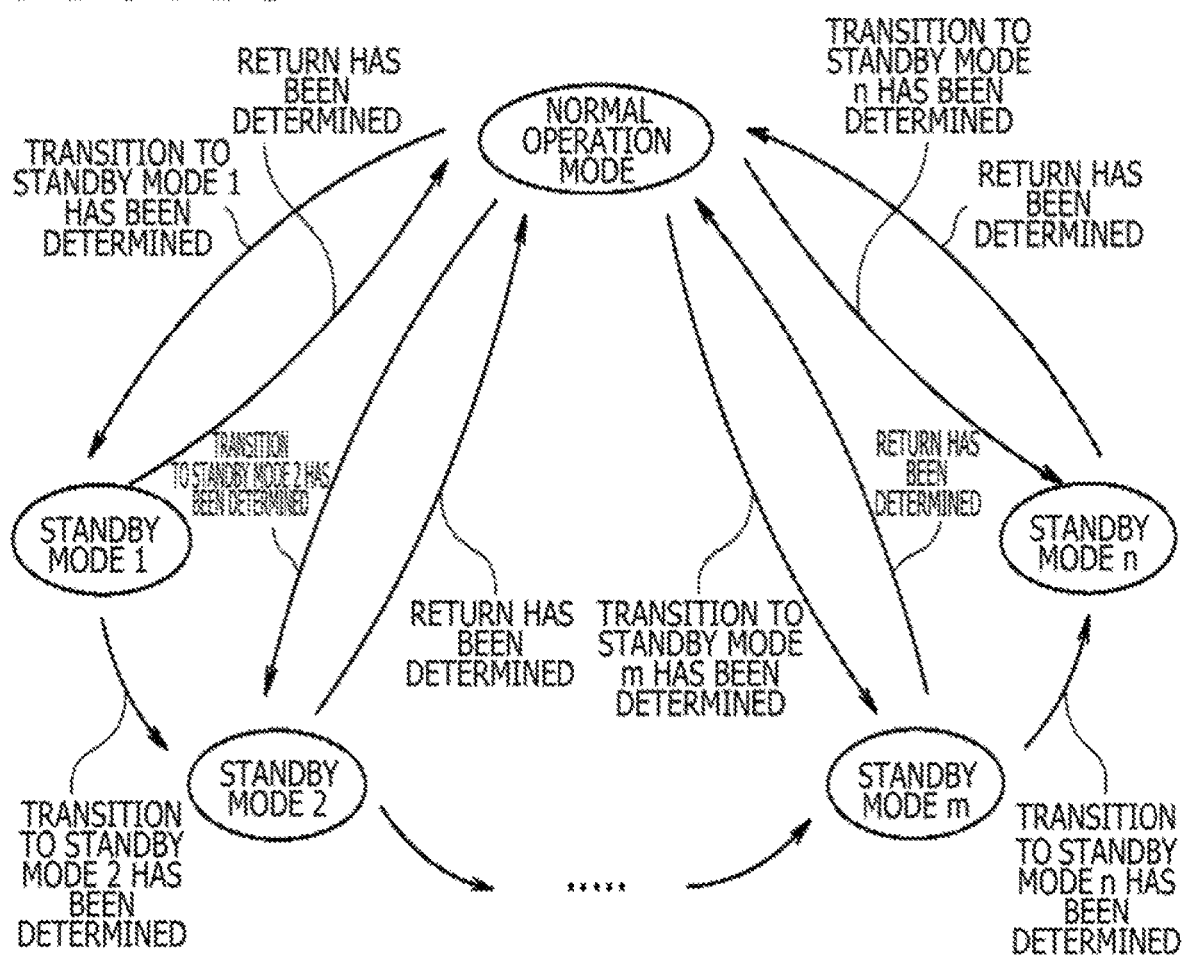
FIG. 10 is a state transition diagram for explaining operation of the second embodiment.

With reference to FIG. 10, a description will next be made about operation of the embodiment configured as described hereinbefore. FIG. 10 is a state transition diagram for explaining the operation of the second embodiment.

In this embodiment, the wireless endoscope 1 is configured to operate in the n+1 kinds of operation modes consisting of the normal operation mode and the standby mode 1 to the standby mode n as illustrated in the state transition diagram of FIG. 10, and transitions are made between the individual operation modes according to the conditions presented in FIG. 10.

Described specifically, the control portion 21 first sets the normal operation mode in FIG. 10 when the power source of the wireless endoscope 1 is turned on. In a determination of transition to the standby mode 1 to a determination of transition to the standby mode n in which a determination is made as to the transition condition in FIG. 10, the placing of the insertion portion 11 outside the body is used as the condition. Further, the condition for the determination of transition to the standby mode 1 is satisfied by the elapse of a predetermined period of time after the insertion portion 11 is left out of use outside the body. Similarly, the condition for the determination of transition to each of the standby mode 2 to the standby mode n is satisfied by the elapse of the predetermined period of time in the state where the insertion portion 11 is left out of use outside the body in the standby mode 1 to a standby mode m or n−1.

In addition, the state transition diagram of FIG. 10 is configured to enable direct transfer from the normal operation mode to the standby mode 1 to the standby mode n by the determination of transition to the standby mode 1 to the determination of transition to the standby mode n. If the surgery time is relatively long and the power consumption needs to be significantly suppressed or in a like case, for example, the state transition diagram may be configured to directly transfer from the normal operation mode to the standby mode 3, the standby mode 4, or the like, for example, according to the level of the battery 24.

In the standby mode 1 to the standby mode n, for example, the time required to return to the normal operation mode is different. If the next surgical procedure allows to spend a long time until returning to the normal operation mode, for example, the state transition diagram may be configured to directly transfer, for example, from the normal operation mode to the standby mode 4 or the like, for example, by designating the next surgical procedure through user's operation.

The return determination satisfies its transition condition if the insertion portion 11 has been put into use for observation from a left-out-of-use state. The return determination is made, for example, based on user's operation at the input operation portion 22, an analysis result by the image analysis portion 29, the detection of movement by the sensor portion 51, or the like.

These determination of transition to the standby mode 1 to determination of transition to the standby mode n are made by the outside-the-body determination portion 46 and the standby mode 1 launch control portion 45a1 to the standby mode n launch control portion 45an. On the other hand, the return determinations are made by the standby mode 1 stop control portion 45b1 to the standby mode n stop control portion 45bn.

The remaining operations are similar to those in the first embodiment.

As described hereinbefore, this embodiment can also bring about similar advantageous effects as in the first embodiment. In addition, this embodiment enables to set a plurality of standby modes, and therefore has a merit that the reduction of power consumption and the shortening of return time can be finely controlled according to the state of use of the wireless endoscope 1.

FIG. 10 illustrates only the example in which the standby mode transitions from the standby mode 1 toward the standby mode 5. However, the state transition diagram may be configured so that among the standby mode 1 to the standby mode 5, for example, the standby mode freely transitions between the individual modes if a predetermined transition condition is satisfied. If the time until the next use of the scope can be empirically grasped to a certain extent, for example, the state transition diagram may be configured so that upon detection of disuse of the scope, the operation mode first transitions from the normal operation mode to the standby mode 4 and then transitions with time from the standby mode 4 toward the standby mode 1.

Modification

Figure 11:
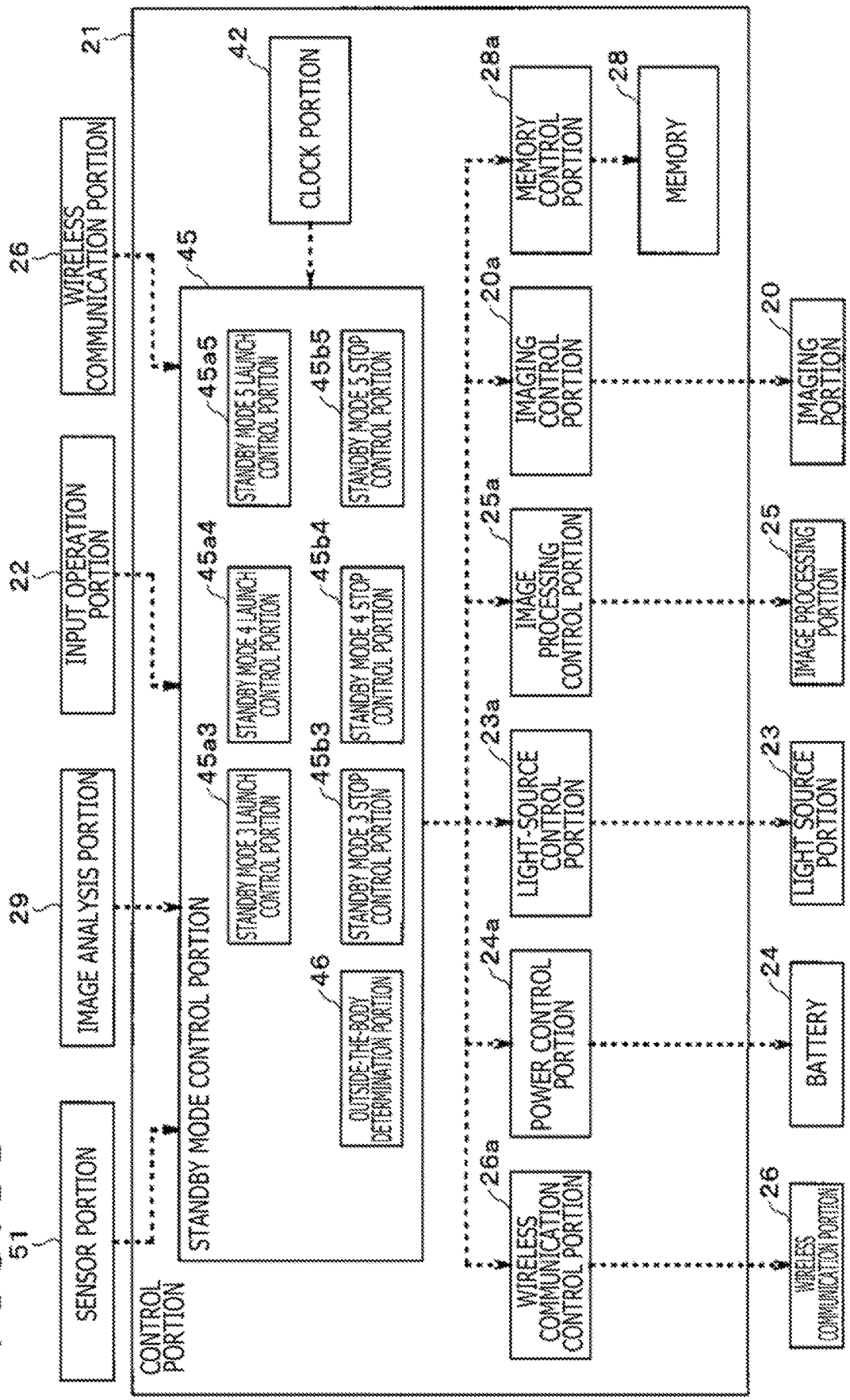
FIG. 11 is a block diagram illustrating a modification of the second embodiment.

FIG. 11 is a block diagram illustrating a modification of the second embodiment. In FIG. 11, the same elements as in FIG. 8 are identified by the same numeral references, and their description is omitted. Standby modes 3 to 5 in this modification are assumed to be, for example, those presented in FIG. 9.

The state transition diagram of FIG. 10 presents only the example in which the standby mode sequentially transitions from the standby mode 1 to the standby mode 5. However, the order of the transitions is not limited as mentioned hereinbefore. This modification presents an example in which the mode, to which the wireless endoscope 1 is to transition, changes according to the transition condition. In FIG. 11, the standby mode control portion 45 of the control portion 21 has, in addition to the function of the outside-the-body determination portion 46, the functions of a standby mode 3 launch control portion 45a3, a standby mode 4 launch control portion 45a4, a standby mode 5 launch control portion 45a5, a standby mode 3 stop control portion 45b3, a standby mode 4 stop control portion 45b4, and a standby mode 5 stop control portion 45b5.

The standby mode 3 launch control portion 45a3 transitions the wireless endoscope 1 from the normal operation mode to the standby mode 3 if disuse of the wireless endoscope 1 is detected in the normal operation mode. In this modification, the standby mode control portion 45 determines the wireless communication environment according to information from the wireless communication portion 26, and based on the determination result, makes the determination of transition to one of the standby mode 4 or 5.

Figure 12:
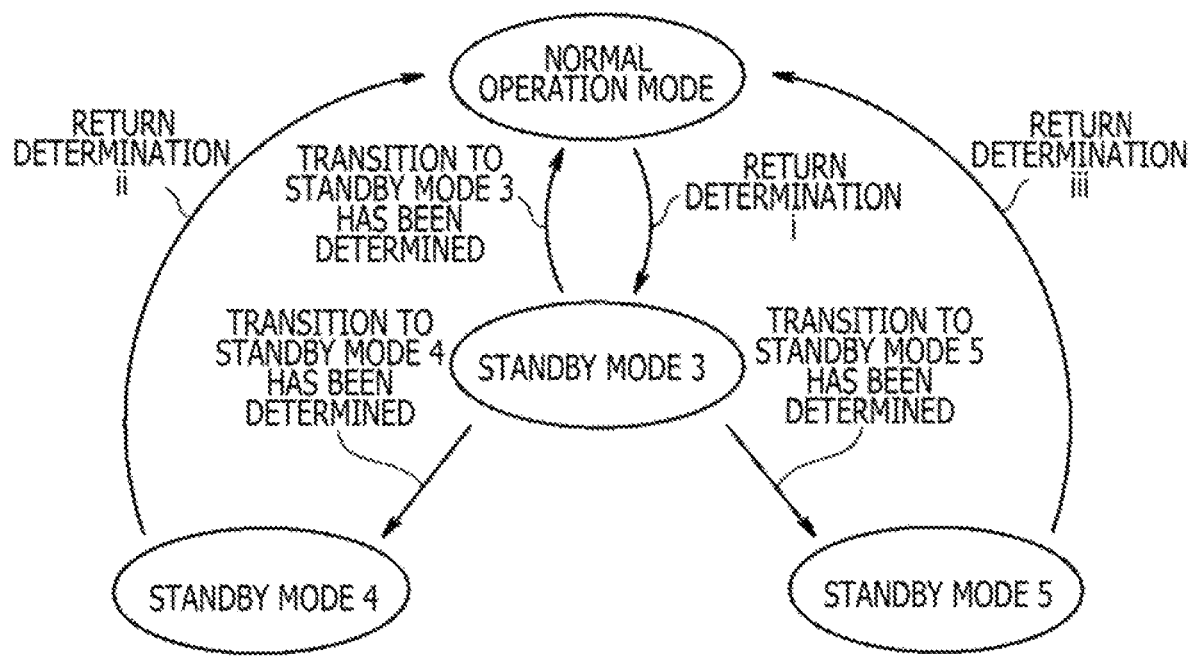
FIG. 12 is a state transition diagram for explaining operation of the modification.
Figure 13:
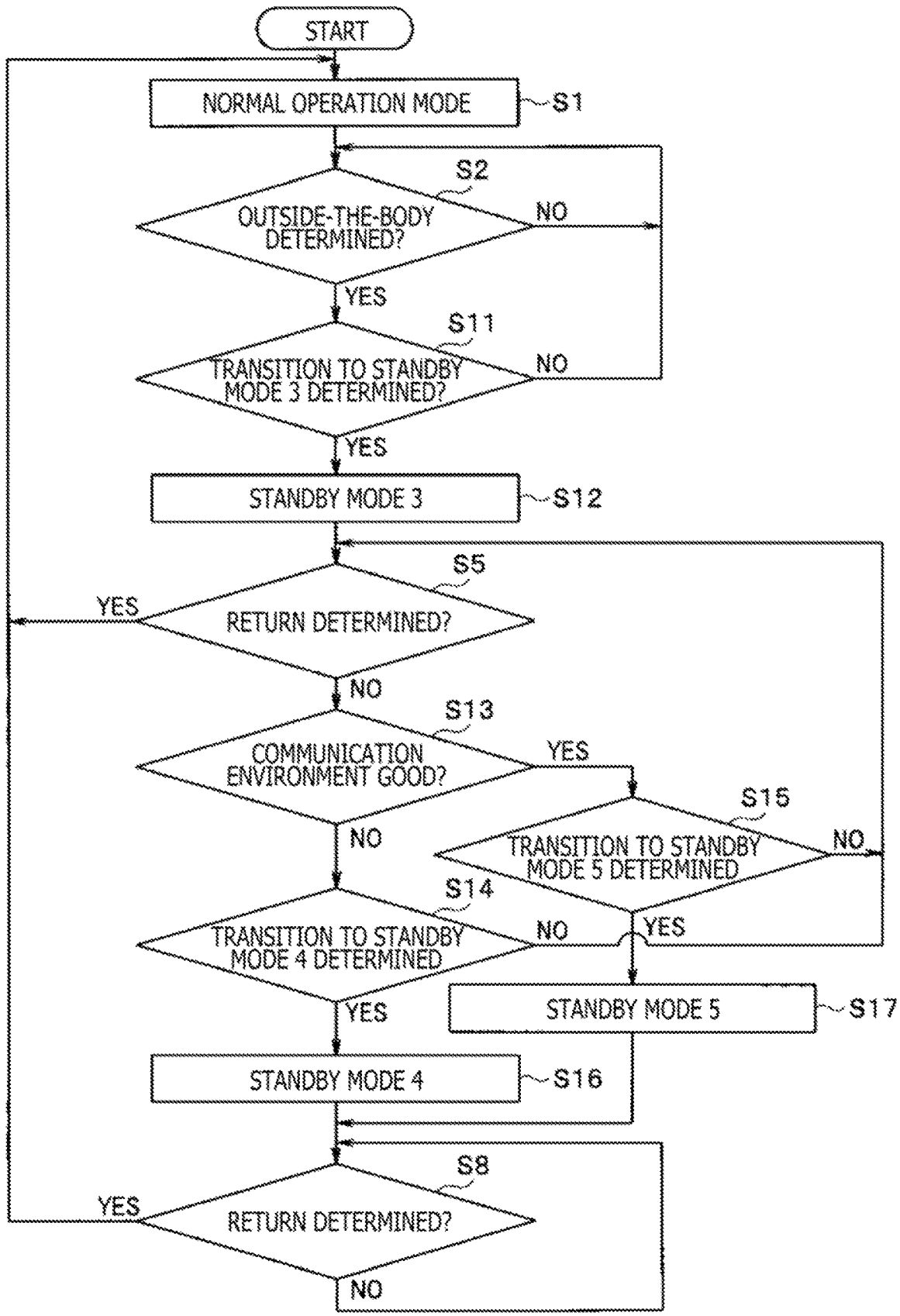
FIG. 13 is a flow chart for explaining the operation of the modification.

FIG. 12 is a state transition diagram for explaining operation of this modification, and FIG. 13 is a flow chart for explaining the operation of this modification. In FIG. 13, the same steps as in FIG. 6 are identified by the same numeral references, and their description is omitted.

If in the normal operation mode, the insertion portion 11 is determined in step S2 to be placed outside the body and is left out of use for a predetermined time outside the body, the standby mode 3 launch control portion 45a3 determines in step S11 that the wireless endoscope 1 is out of use, and causes the wireless endoscope 1 to transition from the normal operation mode to the standby mode 3 in step S12. The return determination in step S5 corresponds to a return determination i in FIG. 12.

The standby mode control portion 45 determines in step S13 whether or not the communication environment is good. As the wireless communication portion 26 has already fed, for example, information regarding error rate as an index, which indicates the communication environment, to the control portion 21, the standby mode control portion 45 may determine the communication environment to be good if the error rate is not greater than a predetermined value, or may determine the communication environment to be poor if the error rate is greater than the predetermined value. As the index indicating the communication environment, various information such as a signal-to-noise (S/N) ratio can be adopted.

If the wireless communication portion 26 cancels the pairing with the processor 30 under a deteriorated communication environment, there is a greater possibility that the channel, which the wireless communication portion 26 has used with the processor 30, may be used by another device, leading to a potential problem that may require a relatively long time for re-pairing. Accordingly, the transition determination is made by the standby mode 5 launch control portion 45a5 if the communication environment is good, and the transition determination is made by the standby mode 4 launch control portion 45a4 if the communication environment is poor.

Under a good communication environment, for example, the standby mode 5 launch control portion 45a5 determines satisfaction of the transition condition in step S15 if the wireless endoscope 1 has been left out of use for the predetermined period of time in the standby mode 3, and causes the wireless endoscope 1 to transition from the standby mode 3 to the standby mode 5 in step S17.

Under a poor communication environment, on the other hand, the standby mode 4 launch control portion 45a4 determines satisfaction of the transition condition in step S14 if the wireless endoscope 1 has been left out of use for the predetermined period of time in the standby mode 3, and causes the wireless endoscope 1 to transition from the standby mode 3 to the standby mode 4 in step S16. The return determination in step S8 corresponds to a return determination ii or iii in FIG. 12.

In this manner, it is possible to prevent the return time to the normal operation mode from becoming relatively long even if the communication environment deteriorates.

Another Modification

Figure 14:
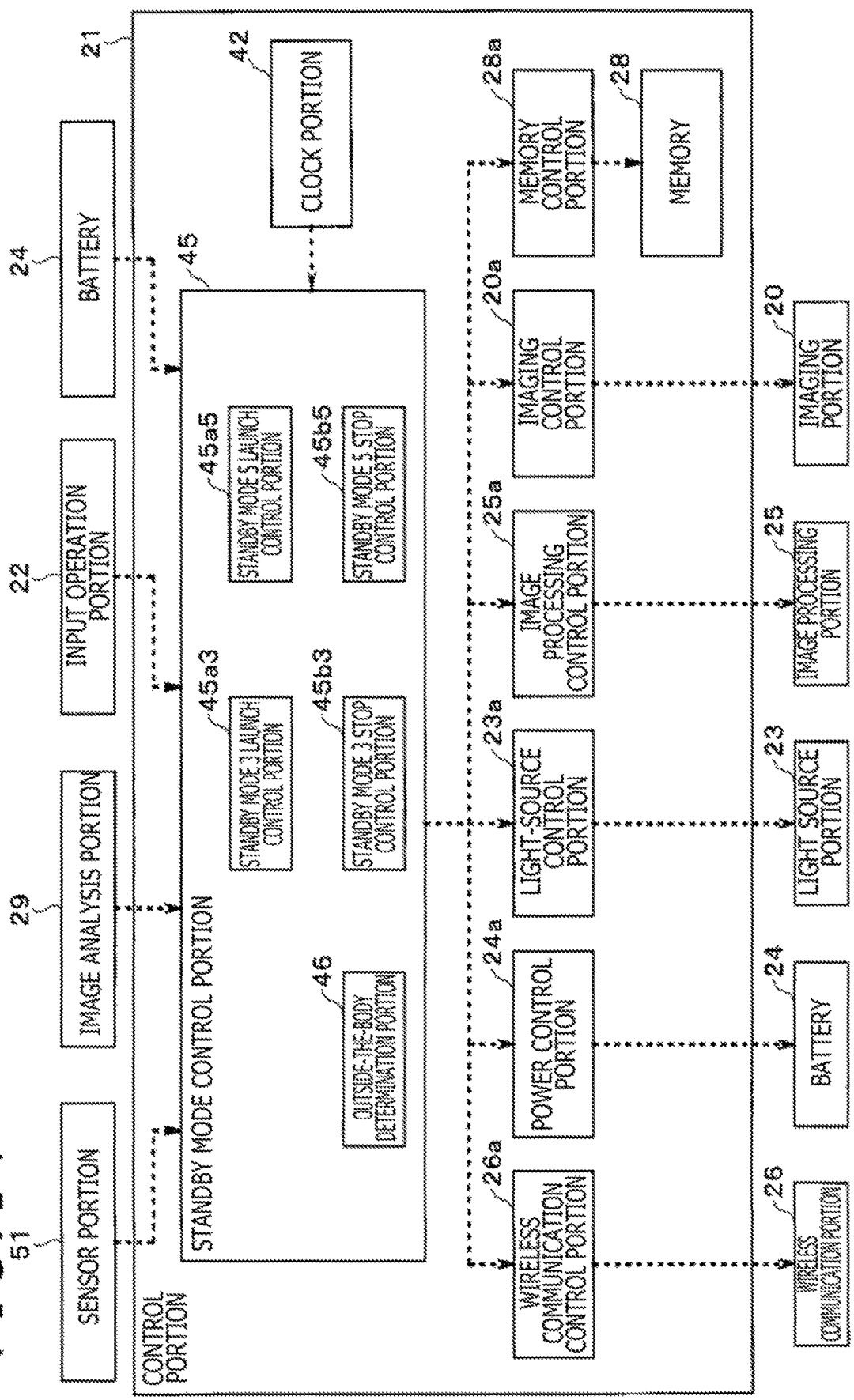
FIG. 14 is a block diagram illustrating another modification of the second embodiment.

FIG. 14 is a block diagram illustrating another modification of the second embodiment. In FIG. 14, the same elements as in FIG. 8 are identified by the same numeral references, and their description is omitted. Standby modes 3 and 5 in this modification are assumed to be, for example, those presented in FIG. 9.

This modification illustrates a specific example that determines a mode to which the wireless endoscope 1 transitions with the battery level included as an additional transition condition. In FIG. 14, the standby mode control portion 45 of the control portion 21 has, in addition to the function of the outside-the-body determination portion 46, the functions of the standby mode 3 launch control portion 45a3, the standby mode 5 launch control portion 45a5, the standby mode 3 stop control portion 45b3, and the standby mode 5 stop control portion 45b5.

If disuse of the wireless endoscope 1 is detected in the normal operation mode, the standby mode control portion 45, based on information regarding the level of the battery 24, makes a determination as to which of the standby mode 3 or the standby mode 5 a transition should be performed. The standby mode 5 stop control portion 45b5 is configured to maintain the standby mode 5 without causing the wireless endoscope 1 to return to the normal operation mode when the level of the battery 24 is extremely low, even if the wireless endoscope 1 is moved or in a like case.

Figure 15:
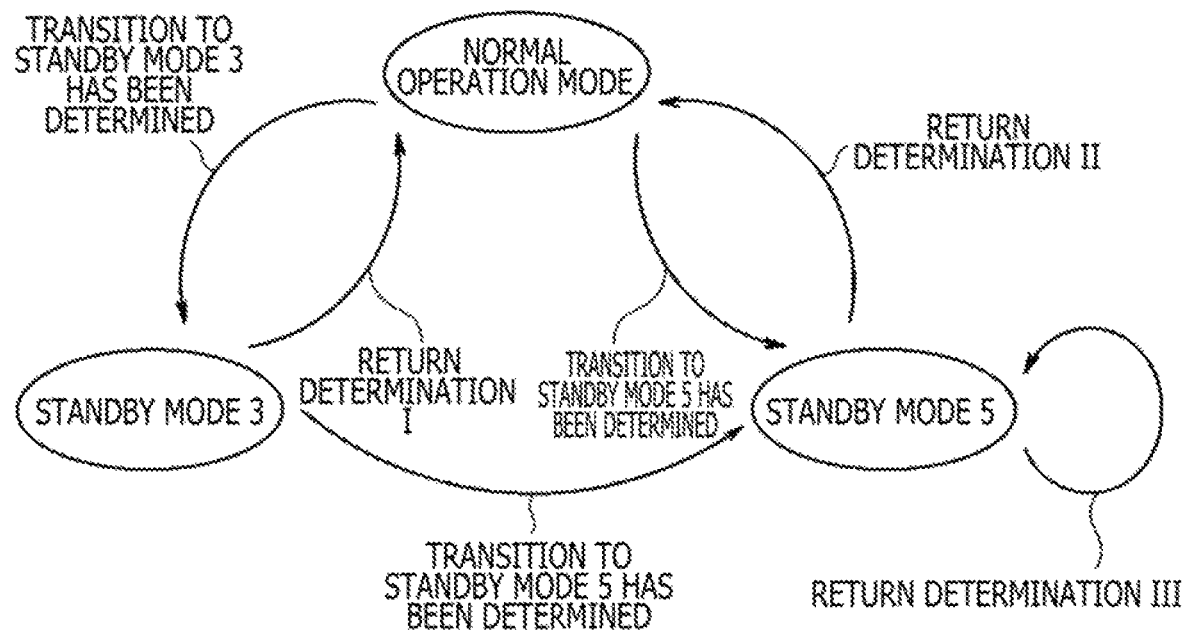
FIG. 15 is a state transition diagram for explaining operation of another modification.
Figure 16:
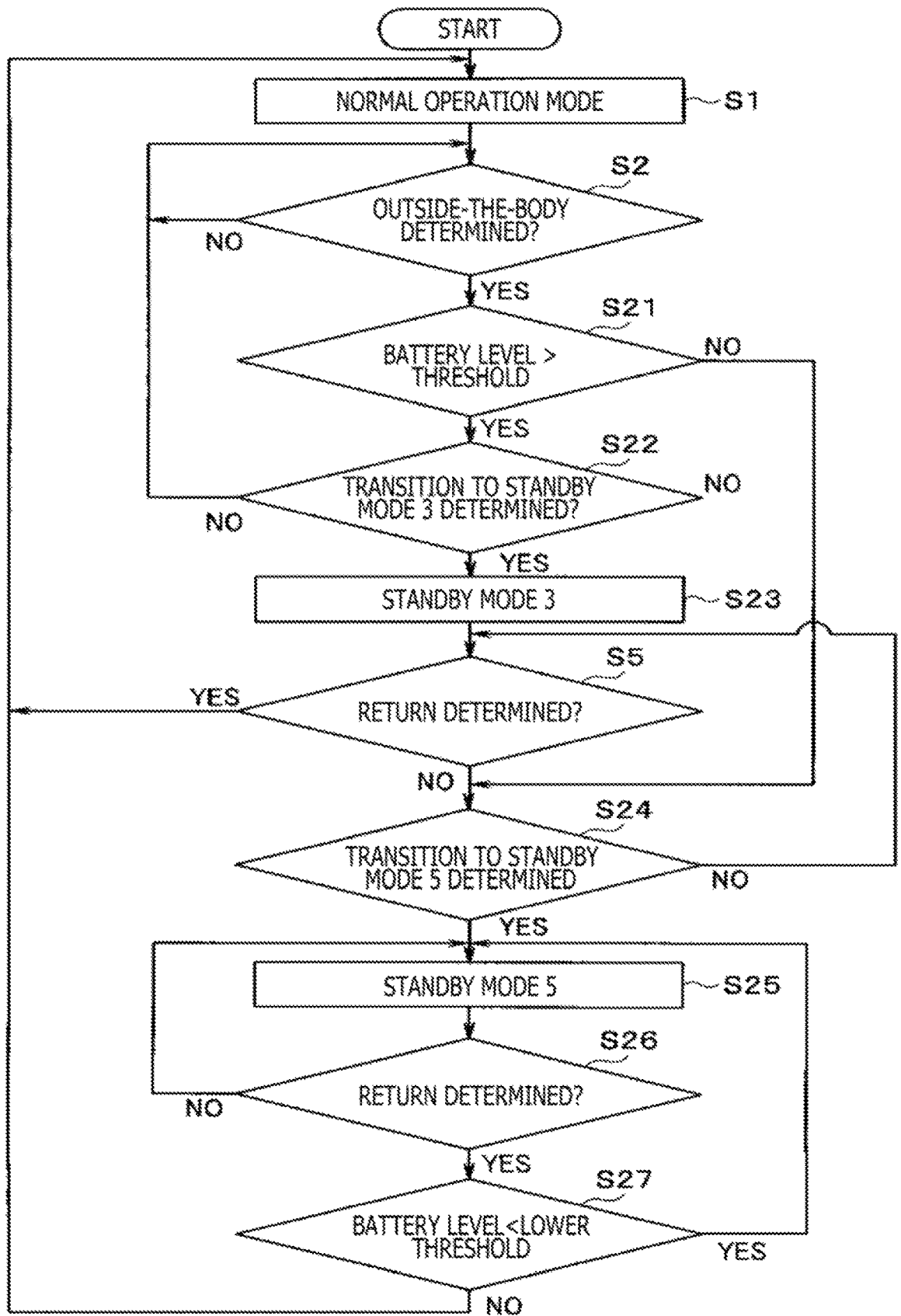
FIG. 16 is a flow chart for explaining the operation of another modification.

FIG. 15 is a state transition diagram for explaining operation of this modification, and FIG. 16 is a flow chart for explaining the operation of this modification. In FIG. 16, the same steps as in FIG. 6 are identified by the same numeral references, and their description is omitted.

If, in the normal operation mode, the insertion portion 11 is determined in step S2 to be placed outside the body and the insertion portion 11 is left out of use for a predetermined period of time outside the body, the standby mode control portion 45 determines in step S21 whether or not the level of the battery 24 is higher than a predetermined threshold. If the level of the battery 24 is relatively low, it may be preferred in some instances to suppress the power consumption rather than paying attention to the return time, so that the wireless endoscope 1 may preferably transition from the normal operation mode to the standby mode 5 rather than to the standby mode 3.

If the standby mode 3 launch control portion 45a3, being limited only to a case where the level of the battery 24 is higher than the predetermined threshold, determines in step S12 that the wireless endoscope 1 has been left out of use for the predetermined period of time, the wireless endoscope 1 is then transitioned from the normal operation mode to the standby mode 3 in step S23. The return determination in step S5 corresponds to a return determination I in FIG. 15.

It is next assumed that, on the other hand, the level of the battery 24 has decreased to the predetermined threshold or further. If the wireless endoscope 1 is determined to have been left out of use for the predetermined period of time in step S24, the standby mode 5 launch control portion 45a5 causes the wireless endoscope 1 to directly transition from the normal operation mode to the standby mode 5 in step S25. As illustrated in FIG. 15, the standby mode 5 is also set in step S25 even if the wireless endoscope 1 is left out of use for the predetermined period of time in the standby mode 3. In the standby mode 5, the standby mode 5 stop control portion 45b5 makes a return determination in step S26. In this case, the standby mode 5 stop control portion 45b5 makes a determination in step S27 as to whether or not the level of the battery 24 has decreased beyond a predetermined lower threshold. If the level of the battery 24 has decreased beyond the predetermined lower threshold, the standby mode 5 stop control portion 45b5 maintains the standby mode 5 without making the return determination as indicated by a return determination III in FIG. 15 even if the wireless endoscope 1 has been moved for use.

If the battery 24 has a level not lower than the predetermined lower threshold, on the other hand, the standby mode 5 stop control portion 45b5 determines satisfaction of the return condition if the wireless endoscope 1 has been moved for use, and causes the wireless endoscope 1 to return to the normal operation mode as indicated by a return determination II in FIG. 15.

As described hereinbefore, the wireless endoscope 1 is transitioned from the normal operation mode to the standby mode 5 to suppress the power consumption in this modification if the use of the wireless endoscope 1 is stopped when the battery level is relatively low. The standby mode 5 is maintained when the battery level is extremely low, even if the use of the wireless endoscope 1 is resumed. In this manner, it is possible to avoid misuse of the wireless endoscope 1 in a state where the battery level is extremely low.

The disclosed technology is not limited strictly to the embodiments and modifications described hereinbefore, and their configuration elements can be embodied through modifications in practice within a scope not departing from the spirit of the disclosed technology. Further, a variety of inventions can be derived by appropriate combinations of plural ones of the configuration elements disclosed in the embodiments and modifications described hereinbefore. For example, some of the entire configuration elements presented in the embodiments and modifications may be omitted. Furthermore, the configuration elements in the different embodiments and modifications may also be combined as desired.

In sum, one aspect of the disclosed technology is directed to an endoscope includes an insertion portion having a light source portion configured to emit illuminating light therefrom when inserted into a body cavity. An imaging portion is configured to capture an image in the body cavity. A transmission portion configured to transmit the image captured by the imaging portion. A battery is configured to supply electric power needed for endoscopic observation. A power control portion is configured to selectively control a supply of electric power to all of the light source portion, the imaging portion, and the transmission portion in a standby mode in which power consumption is reduced compared with a normal operation mode in which a supply of electric power is performed from the battery to all of the light source portion, the imaging portion, and the transmission portion.

In the endoscope, the standby mode is a first standby mode in which a paired state by the transmission portion is maintained, or a second standby mode in which the paired state by the transmission portion is canceled and power supply destinations are selectively decreased to reduce power consumption compared with the first standby mode. The endoscope further comprises a standby mode launch control portion configured to cause a transition between the first standby mode or the second standby mode and the normal operation mode. The standby mode launch control portion is configured to cause a transfer from the normal operation mode to the first or second standby mode according to a level of the battery. The standby mode launch control portion requires as a condition for the transition to the first or second standby mode, that the insertion portion is not inserted in the body cavity. The standby mode launch control portion is configured to detect from the captured image or by a sensor disposed in the insertion portion that the insertion portion is not inserted in the body cavity. The standby mode launch control portion requires as a condition for the transition to the first or second standby mode that the insertion portion has been left out of use for a predetermined period of time outside the body.

The standby mode launch control portion is configured to detect by an amount of movement of the insertion portion in the captured image or a detection result of movement of the insertion portion by the sensor disposed in the insertion portion that the insertion portion has been left out of use for a predetermined period of time outside the body. The standby mode launch control portion requires as a condition for the transition to the second standby mode that the insertion portion has been left out of use for a predetermined period of time outside the body in the first standby mode. The standby mode launch control portion is configured to reduce the power consumption in the first standby mode compared with the normal operation mode without performing stop control of the supply of electric power by the power control portion. The standby mode launch control portion is configured through stop control of the supply of electric power by the power control portion to reduce the power consumption in the first standby mode than the normal operation mode and to reduce the power consumption in the second standby mode as compared with the first standby mode.

The standby mode launch control portion is configured to stop the supply of electric power to the light source portion, the imaging portion, and the transmission portion by controlling the power control portion in the second standby mode. The standby mode launch control portion is configured to divide the first standby mode into a plurality of standby modes of different power consumption, and to cause a transition between at least two of the divided standby modes according to a predetermined transition condition. The endoscope further comprises a standby mode stop control portion configured to cause a return from the first or second standby mode to the normal operation mode upon detection of movement of the insertion portion. The standby mode launch control portion has a storage portion and in the second standby mode is configured to store a receiver identification in the storage portion and to stop the supply of electric power to the light source portion, the imaging portion, and the transmission portion.

Another aspect of the disclosed technology is directed to an endoscope includes an insertion portion having a light source portion configured to emit illuminating light therefrom when inserted into a body cavity. An imaging portion is configured to capture an image in the body cavity. A transmission portion configured to transmit the image captured by the imaging portion. A battery is configured to supply electric power needed for endoscopic observation. A power control portion is configured to selectively control a supply of electric power to all of the light source portion, the imaging portion, and the transmission portion in a standby mode in which power consumption is reduced compared with a normal operation mode in which a supply of electric power is performed from the battery to all of the light source portion, the imaging portion, and the transmission portion. A processor is configured to receive the captured image by performing communication with the transmission portion.

A further aspect of the disclosed technology a method of operating an endoscope system using a non-transitory image processing program product having computer program code encoded thereon that when executed by a processor of a computer causes the computer to perform the operations of power supply in the endoscope system, the method comprising: transitioning to a standby mode in which power supply destinations are selectively decreased from a light source portion, an imaging portion, a transmission portion, and a plurality of circuit portions to reduce power consumption compared with a normal operation mode in which a supply of electric power is performed from a battery to all of the light source portion, the imaging portion, the transmission portion, and the circuit portions, and returning from the standby mode to the normal operation mode.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope comprising:
an insertion portion of a body of the endoscope having a light source configured to emit illuminating light when inserted into a body cavity;
an imaging device configured to capture an image in the body cavity;
a transmitter/receiver configured to transmit the captured image to an external device;
a battery configured to supply electric power needed for endoscopic observation; and
a power control processor configured to:
selectively control a supply of electric power from the battery to all of the light source, the imaging device, and the transmitter/receiver in a standby mode in which power consumption is reduced compared with a normal operation mode in which the supply of electric power is performed from the battery to all of the light source, the imaging device, and the transmitter/receiver, the standby mode including a first standby mode and a second standby mode;
determine whether the insertion portion is located inside the body cavity; and
in response to determining that the insertion portion is not located inside the body cavity, perform the first standby mode that reduces the supply of electric power from the battery as compared to the normal operation mode for a predetermined period of time after ending the normal operation mode, and perform the second standby mode that reduces the supply of electric power from the battery as compared to the first standby mode to supply a minimum amount of electric power necessary to operate one of the imaging device, the transmitter/receiver, and the insertion portion for more than the predetermined period of time.

2. The endoscope of claim 1, wherein in the first standby mode, a paired state by the transmitter/receiver is maintained, and in the second standby mode, the paired state by the transmitter/receiver is canceled and power supply destinations are selectively decreased to reduce power consumption compared with the first standby mode.

3. The endoscope of claim 2, wherein the power control processor is configured to cause a transition between the first standby mode or the second standby mode, and the normal operation mode.

4. The endoscope of claim 3, wherein the power control processor performs the transition to the first standby mode or the second standby mode when the insertion portion is not inserted in the body cavity.

5. The endoscope of claim 4, wherein the power control processor is configured to detect from the captured image or by a sensor disposed in the insertion portion that the insertion portion is not inserted in the body cavity.

6. The endoscope of claim 5, wherein the power control processor is configured to detect that the insertion portion has been removed from use for a predetermined period of time outside the body based on an amount of movement of the insertion portion in the captured image or a detection result of movement of the insertion portion by the sensor disposed in the insertion portion.

7. The endoscope of claim 5, wherein the power control processor performs the transition to the second standby mode when the insertion portion has been removed from use for a predetermined period of time outside the body in the first standby mode.

8. The endoscope of claim 7, wherein the power control processor is configured to stop the supply of electric power to the light source, the imaging device, and the transmitter/receiver in the second standby mode.

9. The endoscope of claim 3, wherein the power control processor performs the transition to the first standby mode or the second standby mode when the insertion portion has been removed from use for a predetermined period of time outside the body.

10. The endoscope of claim 3, wherein the power control processor is configured to reduce the power consumption in the first standby mode compared with the normal operation mode without performing stop control of the supply of electric power.

11. The endoscope of claim 10, wherein the power control processor includes a memory, and in the second standby mode the power control processor is configured to store a receiver identification in the memory and to stop the supply of electric power to the light source, the imaging device, and the transmitter/receiver.

12. The endoscope of claim 3, wherein the power control processor is configured, through stop control of the supply of electric power by the power control processor, to reduce the power consumption in the first standby mode than the normal operation mode and to reduce the power consumption in the second standby mode as compared with the first standby mode.

13. The endoscope of claim 3, wherein the power control processor is configured to divide the first standby mode into a plurality of standby modes of different power consumption, and to cause a transition between at least two of the divided standby modes according to a predetermined transition condition.

14. The endoscope of claim 3, wherein the power control processor is configured to cause a return from the first standby mode or the second standby mode to the normal operation mode upon detection of movement of the insertion portion.

15. The endoscope of claim 2, wherein the power control processor is configured to cause a transfer from the normal operation mode to the first standby mode or the second standby mode according to a power level of the battery.

16. An endoscope system comprising:
the endoscope of claim 1; and
an endoscope processor configured to receive the captured image by performing communication with the transmitter/receiver.

17. The endoscope system of claim 16, wherein in the first standby mode, a paired state by the transmitter/receiver is maintained, and in the second standby mode, the paired state by the transmitter/receiver is canceled and power supply destinations are selectively decreased to reduce power consumption compared with the first standby mode.

18. A method of operating an endoscope system using a non-transitory computer readable storage medium storing an image processing program having computer program code that when executed by a processor of a computer causes the computer to perform operations of power supply in the endoscope system, the method comprising:
transitioning to a standby mode in which power supply destinations are selectively decreased from a light source, an imaging device, a transmitter/receiver, and a plurality of circuits to reduce power consumption as compared with a normal operation mode in which a supply of electric power is performed from a battery to all of the light source, the imaging device, the transmitter/receiver, and the plurality of circuits;

determining whether an insertion portion of an endoscope of the endoscope system is located inside a body cavity;

in response to determining that the insertion portion is not located inside the body cavity, performing the first standby mode that reduces the supply of electric power from the battery as compared to the normal operation mode for a predetermined period of time after ending the normal operation mode, and performing the second standby mode that reduces the supply of electric power from the battery as compared to the first standby mode to supply a minimum amount of electric power necessary to operate one of the imaging device, the transmitter/receiver, and the insertion portion for more than the predetermined period of time; and returning from the standby mode to the normal operation mode.

19. The method of claim 18, wherein in the first standby mode, a paired state by the transmitter/receiver is maintained, and in the second standby mode, the paired state by the transmitter/receiver is canceled and the power supply destinations are selectively decreased to reduce power consumption compared with the first standby mode.

\* \* \* \* \*